US012774344B2

(12) United States Patent
Wang et al.

(10) Patent No.: US 12,774,344 B2
(45) **Date of Patent: *Oct. 27, 2026**

(54) ANTI-CD73 ANTIBODY AND USE THEREOF

(71) Applicant: Akeso Biopharma, Inc, Zhongshan (CN)

(72) Inventors: Zhongmin Wang, Zhongshan (CN); Peng Zhang, Zhongshan (CN); Baiyong Li, Zhongshan (CN); Yu Xia, Zhongshan (CN)

(73) Assignee: Akeso Biopharma, Inc., Zhongshan (CN)

( * ) Notice: Subject to any disclaimer, the term of this patent is extended or adjusted under 35 U.S.C. 154(b) by 874 days.

This patent is subject to a terminal disclaimer.

(21) Appl. No.: 17/996,841

(22) PCT Filed: Apr. 22, 2021

(86) PCT No.: PCT/CN2021/088987

§ 371 (c)(1),
(2) Date: Oct. 21, 2022

(87) PCT Pub. No.: WO2021/213466

PCT Pub. Date: Oct. 28, 2021

(65) Prior Publication Data

US 2023/0159655 A1 May 25, 2023

(30) Foreign Application Priority Data

Apr. 22, 2020 (CN) ........................ 202010324782.X
Oct. 23, 2020 (CN) ......................... 202011152518.9

(51) Int. Cl.
*A61K 39/395* (2006.01)
*A61K 47/68* (2017.01)
*C07K 16/28* (2006.01)
*C07K 16/40* (2006.01)

(52) U.S. Cl.
CPC ...... *C07K 16/2896* (2013.01); *A61K 47/6849* (2017.08); *A61K 47/6871* (2017.08); *C07K 16/40* (2013.01); *C07K 2317/24* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS 4,816,567 A 3/1989 Cabilly et al.
2016/0129108 A1 5/2016 Sachsenmeier et al.
2017/0253665 A1 9/2017 Lonberg et al.
2018/0237536 A1 8/2018 Perrot et al.
2019/0031766 A1 1/2019 Prinz et al.
2019/0077873 A1 3/2019 Griffin et al.
2020/0071404 A1 3/2020 Sato et al.
2020/0148781 A1 5/2020 Zeidler et al.
2020/0332005 A1 10/2020 Wang et al.

FOREIGN PATENT DOCUMENTS

CN 106852149 A 6/2017
CN 107001474 A 8/2017
CN 109154611 A 1/2019
CN 109476755 A 3/2019
CN 110072891 A 7/2019
CN 110753703 A 2/2020
CN 110785187 A 2/2020
JP 2023-522365 A 5/2023
KR 10-2017-0070077 A 6/2017
WO 2016/055609 A1 4/2016
WO 2016/075099 A1 5/2016
WO 2016/081748 A2 5/2016
WO 2016/131950 A1 8/2016
WO 2017/064043 A1 4/2017
WO 2017/152085 A1 9/2017
WO 2018/137598 A1 8/2018
WO 2018/237157 A1 12/2018
WO 2019/173291 A1 9/2019
WO 2021/213475 A1 10/2021

OTHER PUBLICATIONS

Almagro & Fransson, Frontiers in Bioscience 2008; 13:1619-33 (Year: 2008).*
Rudikoff et al. (Proc Natl Acad Sci USA 1982 vol. 79 p. 1979) (Year: 1982).*
MacCallum et al. J. Mol. Biol. (1996) 262, 732-745 (Year: 1996).*
Pascalis et al. (The Journal of Immunology (2002) 169, 3076-3084) (Year: 2002).*
Casset et al. (BBRC 2003, 307:198-205) (Year: 2003).*
Vajdos et al. (J. Mol. Biol. (2002) 320, 415-428) (Year: 2002).*
Chen et al. (J. Mol. Bio. (1999) 293, 865-881) (Year: 1999).*
Wu et al. (J. Mol. Biol. (1999) 294, 151-162) (Year: 1999).*
Padlan et al. (PNAS 1989, 86:5938-5942) (Year: 1989).*
Lamminmaki et al. (JBC 2001, 276:36687-36694) (Year: 2001).*
Martin et al (Journal of the National Cancer Institute, vol. 92, No. 14: pp. 1126-1135, Jul. 19, 2000) (Year: 2000).*
Apantaku et al. (Breast cancer diagnosis and screening, American Family Physician 2000) (Year: 2000).*
International Search Report of PCT/CN2021/088987, Jul. 26, 2021.
Antonioli et al., “Immunity, inflammation and cancer: a leading role for adenosine” Nat Rev Cancer 13:842-857 (2013).

(Continued)

*Primary Examiner* — Meera Natarajan
(74) *Attorney, Agent, or Firm* — Medler Ferro Woodhouse & Mills PLLC

(57) ABSTRACT

Provided in the present invention are an anti-CD73 antibody and the use thereof. Specifically, a heavy chain variable region of the antibody contains HCDR1 to HCDR3 having amino acid sequences as shown in SEQ ID NOs: 15-17, respectively. Furthermore, a light chain variable region of the antibody contains LCDR1 to LCDR3 having amino acid sequences as shown in SEQ ID NOs: 18-20, respectively.

19 Claims, 3 Drawing Sheets

Specification includes a Sequence Listing.

(56) References Cited

OTHER PUBLICATIONS

Chothia & Lesk, Canonical structures for the hypervariable regions of immunoglobulins J. Mol. Biol. 196:901-917 (1987).
Chothia et al., "Conformations of immunoglobulin hypervariable regions" Nature 342:878-883 (1989).
Clark, "Antibody humanization: a case of the 'Emperor's new clothes'?" J. Immunol. Today 21(8): 397-402 (2000).
Ehrenmann et al., "IMGT/3Dstructure-DB and IMGT/DomainGapAlign: a database and a tool for immunoglobulins or antibodies, T cell receptors, MHC, IgSF and MhcSF" Nucleic acids research 38(suppl_1): D301-D307 (2009).
Hage et al., "Crystals of a 1:1 Complex Between Human Interleukin-4 and the Extracellular Domain of Its Receptor Alpha Chain" Eur. J. Biochem. 258(2):831-836 (1998).
Köhler & Mistein, "Continuous cultures of fused cells secreting antibody of predefined specificity" Nature 256(5517): 495 (1975).
Jones et al., "Replacing the complementarity-determining regions in a human antibody with those from a mouse" Nature 321:522-525 (1986).
Presta, "Antibody engineering" Curr. Op. Struct. Biol. 2:593-596 (1992).
Regateiro et al., "CD73 and adenosine generation in the creation of regulatory microenvironments" Clin. Exp. Immunol. 171:1-7 (2013).
Synnestvedt et al., "Ecto-5'-nucleotidase (CD73) regulation by hypoxia-inducible factor-1 mediates permeability changes in intestinal epithelia" J. Clin. Invest. 110:993-1002 (2002).
Zimmermann, "5'-Nucleotidase: molecular structure and functional aspects" Biochem J. 285:345-365 (1992).
Riechmann et al., "Reshaping human antibodies for therapy," Nature 332:323-327 (1988).
Extended European Search Report and Written Opinion in European Patent Application No. 21792447.1, mailed Aug. 5, 2024.
Office Action issued in KR 10-2022-7040578, dated Jun. 20, 2025.
Office Action issued in JP 2022-563881, dated Jul. 1, 2025.
Action issued in EP 21792447.1, dated Sep. 1, 2025.
Office Action issued in JP 2023-548995, mailed Dec. 9, 2025.
Dresbuxelimab, CAS SciFinder, 2550560-20-6, accessed Jun. 30, 2026.
Office Action issued by the European Patent Office dated Jun. 2, 2026, in European Patent Application 21792447.1.
Office Action issued by the Intellectual Property Office Of The Philippines Bureau Of Patents dated Jun. 4, 2026, in Filipino Patent Application 1/2022/552786.
Office Action issued by the Intellectual Property Office of Singapore dated May 2, 2026, in Singaporean Patent Application 11202254279K.

* cited by examiner

SEQUENCE LISTING

<160> NUMBER OF SEQ ID NOS: 22

<210> SEQ ID NO 1
<211> LENGTH: 363
<212> TYPE: DNA
<213> ORGANISM: Artificial Sequence
<220> FEATURE:
<223> OTHER INFORMATION: Synthetic Artificial Sequence

<400> SEQUENCE: 1
gaggtgcagc tgcagcagtc cggaccagag ctggtgaagc ctggcgcctc catgcggatg 60
tcttgtaagg cctctggcta cagcttcacc ggctatacaa tgaactgggt gaagcagtct 120
cacggcaaga atctggagtg gatcggcctg atcaaccctt acaatgccgg caccagctat 180
aaccagaagt ttaagggcaa ggccaccctg acagtggaca agagctcctc taccgcctac 240
atggagctgc tgtccctgac atctgaggat agcgccgtgt actattgcgc ccggtccgag 300
tacagatatg gcggcgacta ctttgattat tggggccagg gcaccacact gacagtgagc 360
tcc 363

<210> SEQ ID NO 2
<211> LENGTH: 121
<212> TYPE: PRT
<213> ORGANISM: Artificial Sequence
<220> FEATURE:
<223> OTHER INFORMATION: Synthetic Artificial Sequence

<400> SEQUENCE: 2

Glu Val Gln Leu Gln Gln Ser Gly Pro Glu Leu Val Lys Pro Gly Ala
1 5 10 15

Ser Met Arg Met Ser Cys Lys Ala Ser Gly Tyr Ser Phe Thr Gly Tyr
20 25 30

Thr Met Asn Trp Val Lys Gln Ser His Gly Lys Asn Leu Glu Trp Ile
35 40 45

Gly Leu Ile Asn Pro Tyr Asn Ala Gly Thr Ser Tyr Asn Gln Lys Phe
50 55 60

Lys Gly Lys Ala Thr Leu Thr Val Asp Lys Ser Ser Ser Thr Ala Tyr
65 70 75 80

Met Glu Leu Leu Ser Leu Thr Ser Glu Asp Ser Ala Val Tyr Tyr Cys
85 90 95

Ala Arg Ser Glu Tyr Arg Tyr Gly Gly Asp Tyr Phe Asp Tyr Trp Gly
100 105 110

Gln Gly Thr Thr Leu Thr Val Ser Ser
115 120

<210> SEQ ID NO 3
<211> LENGTH: 339
<212> TYPE: DNA
<213> ORGANISM: Artificial Sequence
<220> FEATURE:
<223> OTHER INFORMATION: Synthetic Artificial Sequence

<400> SEQUENCE: 3
gacatcgtga tgacccagtc tccaagctcc ctggcaatga gcgtgggaca gaaggtgaca 60
atgtcttgta agtctagcca gagcctgctg aactcctcta atcagaagaa ctacctggcc 120
tggtatcagc agaagccagg ccagtctccc aagctgctgg tgtactttgc cagcaccagg 180
gagtccggag tgcctgacag attcatcggc tccggctctg gcacagactt caccctgaca 240
atcagctccg tgcaggcaga ggacctggca gattatttct gccagcagca ctacgacacc 300
ccttatacat ttggcggcgg caccaagctg gagatcaag 339

<210> SEQ ID NO 4
<211> LENGTH: 113
<212> TYPE: PRT
<213> ORGANISM: Artificial Sequence
<220> FEATURE:
<223> OTHER INFORMATION: Synthetic Artificial Sequence

<400> SEQUENCE: 4

Asp Ile Val Met Thr Gln Ser Pro Ser Ser Leu Ala Met Ser Val Gly
1 5 10 15

Gln Lys Val Thr Met Ser Cys Lys Ser Ser Gln Ser Leu Leu Asn Ser
20 25 30

Ser Asn Gln Lys Asn Tyr Leu Ala Trp Tyr Gln Gln Lys Pro Gly Gln
35 40 45

Ser Pro Lys Leu Leu Val Tyr Phe Ala Ser Thr Arg Glu Ser Gly Val
50 55 60

Pro Asp Arg Phe Ile Gly Ser Gly Ser Gly Thr Asp Phe Thr Leu Thr
65 70 75 80

Ile Ser Ser Val Gln Ala Glu Asp Leu Ala Asp Tyr Phe Cys Gln Gln
85 90 95

His Tyr Asp Thr Pro Tyr Thr Phe Gly Gly Gly Thr Lys Leu Glu Ile
100 105 110

Lys

<210> SEQ ID NO 5
<211> LENGTH: 363
<212> TYPE: DNA
<213> ORGANISM: Artificial Sequence
<220> FEATURE:
<223> OTHER INFORMATION: Synthetic Artificial Sequence

<400> SEQUENCE: 5
caggtgcagc tgcagcagtc tggagcagag gtggtgaagc caggagcctc tatgaagatg 60
agctgtaagg ccagcggcta ctccttcacc ggctatacaa tgaactgggt gaagcaggcc 120
cacggccaga atctggagtg gatcggcctg atcaaccctt acaatgccgg cacctcttat 180
aaccagaagt ttcagggcaa ggccaccctg acagtggaca agtccacctc tacagcctac 240
atggagctga gctccctgcg gagcgaggat acagccgtgt actattgcgc ccggtccgag 300
tacagatatg gcggcgacta ctttgattat tggggccagg gcaccacact gaccgtgtct 360
agc 363

<210> SEQ ID NO 6
<211> LENGTH: 121
<212> TYPE: PRT
<213> ORGANISM: Artificial Sequence
<220> FEATURE:
<223> OTHER INFORMATION: Synthetic Artificial Sequence

<400> SEQUENCE: 6

Gln Val Gln Leu Gln Gln Ser Gly Ala Glu Val Val Lys Pro Gly Ala
1 5 10 15

Ser Met Lys Met Ser Cys Lys Ala Ser Gly Tyr Ser Phe Thr Gly Tyr
20 25 30

Thr Met Asn Trp Val Lys Gln Ala His Gly Gln Asn Leu Glu Trp Ile
35 40 45

```
Gly Leu Ile Asn Pro Tyr Asn Ala Gly Thr Ser Tyr Asn Gln Lys Phe
    50                  55                  60

Gln Gly Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Glu Tyr Arg Tyr Gly Gly Asp Tyr Phe Asp Tyr Trp Gly
            100                 105                 110

Gln Gly Thr Thr Leu Thr Val Ser Ser
        115                 120


<210> SEQ ID NO 7
<211> LENGTH: 339
<212> TYPE: DNA
<213> ORGANISM: Artificial Sequence
<220> FEATURE:
<223> OTHER INFORMATION: Synthetic Artificial Sequence

<400> SEQUENCE: 7

gacatcgtga tgacccagtc cccaagctcc ctggcaatgt ctgtgggaga gagggtgaca      60

atgtcctgta agtctagcca gtctctgctg aactcctcta atcagaagaa ctacctggcc     120

tggtatcagc agaagcccgg ccaggcccct aagctgctgg tgtactttgc ctctaccagg     180

gagagcggag tgccagacag attctctggc agcggctccg gcacagactt caccctgaca     240

atcagctccg tgcaggcaga ggacctggca gattatttct gccagcagca ctacgatacc     300

ccctatacat ttggcggcgg caccaagctg gagatcaag                            339


<210> SEQ ID NO 8
<211> LENGTH: 113
<212> TYPE: PRT
<213> ORGANISM: Artificial Sequence
<220> FEATURE:
<223> OTHER INFORMATION: Synthetic Artificial Sequence

<400> SEQUENCE: 8

Asp Ile Val Met Thr Gln Ser Pro Ser Ser Leu Ala Met Ser Val Gly
1               5                   10                  15

Glu Arg Val Thr Met Ser Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ala Pro Lys Leu Leu Val Tyr Phe Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Asp Thr Pro Tyr Thr Phe Gly Gly Gly Thr Lys Leu Glu Ile
            100                 105                 110

Lys


<210> SEQ ID NO 9
<211> LENGTH: 363
<212> TYPE: DNA
<213> ORGANISM: Artificial Sequence
<220> FEATURE:
<223> OTHER INFORMATION: Synthetic Artificial Sequence

<400> SEQUENCE: 9
```

```
caggtgcagc tggtgcagtc tggagcagag gtggtgaagc caggagcctc tgtgaaggtg     60

agctgtaagg ccagcggcta ctccttcacc ggctatacaa tgaactgggt gaggcaggca    120

ccaggacaga atctggagtg gatcggcctg atcaaccctt acaatgccgg cacctcttat    180

aaccagaagt ttcagggcaa ggtgaccctg acagtggaca agtccacctc tacagcctac    240

atggagctga gctccctgcg gagcgaggat acagccgtgt actattgcgc ccggtccgag    300

tacagatatg gcggcgacta ctttgattat tggggccagg gcaccacact gaccgtgtct    360

agc                                                                  363


<210> SEQ ID NO 10
<211> LENGTH: 121
<212> TYPE: PRT
<213> ORGANISM: Artificial Sequence
<220> FEATURE:
<223> OTHER INFORMATION: Synthetic Artificial Sequence

<400> SEQUENCE: 10

Gln Val Gln Leu Val Gln Ser Gly Ala Glu Val Val Lys Pro Gly Ala
1               5                   10                  15

Ser Val Lys Val Ser Cys Lys Ala Ser Gly Tyr Ser Phe Thr Gly Tyr
            20                  25                  30

Thr Met Asn Trp Val Arg Gln Ala Pro Gly Gln Asn Leu Glu Trp Ile
        35                  40                  45

Gly Leu Ile Asn Pro Tyr Asn Ala Gly Thr Ser Tyr Asn Gln Lys Phe
    50                  55                  60

Gln Gly Lys Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Glu Tyr Arg Tyr Gly Gly Asp Tyr Phe Asp Tyr Trp Gly
            100                 105                 110

Gln Gly Thr Thr Leu Thr Val Ser Ser
        115                 120


<210> SEQ ID NO 11
<211> LENGTH: 339
<212> TYPE: DNA
<213> ORGANISM: Artificial Sequence
<220> FEATURE:
<223> OTHER INFORMATION: Synthetic Artificial Sequence

<400> SEQUENCE: 11

gacatcgtga tgacccagtc cccaagctcc ctggccgtgt ctgtgggaga gcgggtgaca     60

atctcctgta agtctagcca gtctctgctg aactcctcta atcagaagaa ctacctggcc    120

tggtatcagc agaagcccgg ccaggcccct aagctgctga tctacttcgc ctctaccagg    180

gagagcggag tgccagacag attctctggc agcggctccg gcacagactt caccctgaca    240

atcagctccg tgcaggcaga ggacgtggca gattactatt gccagcagca ctacgatacc    300

ccctatacat ttggcggcgg caccaagctg gagatcaag                           339


<210> SEQ ID NO 12
<211> LENGTH: 113
<212> TYPE: PRT
<213> ORGANISM: Artificial Sequence
<220> FEATURE:
<223> OTHER INFORMATION: Synthetic Artificial Sequence
```

<400> SEQUENCE: 12

Asp Ile Val Met Thr Gln Ser Pro Ser Ser Leu Ala Val Ser Val Gly
1 5 10 15

Glu Arg Val Thr Ile Ser Cys Lys Ser Ser Gln Ser Leu Leu Asn Ser
20 25 30

Ser Asn Gln Lys Asn Tyr Leu Ala Trp Tyr Gln Gln Lys Pro Gly Gln
35 40 45

Ala Pro Lys Leu Leu Ile Tyr Phe Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Val Gln Ala Glu Asp Val Ala Asp Tyr Tyr Cys Gln Gln
85 90 95

His Tyr Asp Thr Pro Tyr Thr Phe Gly Gly Gly Thr Lys Leu Glu Ile
100 105 110

Lys

<210> SEQ ID NO 13
<211> LENGTH: 339
<212> TYPE: DNA
<213> ORGANISM: Artificial Sequence
<220> FEATURE:
<223> OTHER INFORMATION: Synthetic Artificial Sequence

<400> SEQUENCE: 13
gacatcgtga tgacccagtc cccaagctcc ctggccgtgt ctgtgggaga gcgggtgaca 60
atctcctgta agtctagcca gtctctgctg aactcctcta atcagaagaa ctacctggcc 120
tggtatcagc agaagcccgg ccaggcccct aagctgctga tctacttcgc ctctaccagg 180
gagagcggag tgccagacag attctctggc agcggctccg gcacagactt caccctgaca 240
atcagctccc tgcaggcaga ggacgtggcc gtgtactatt gccagcagca ctacgatacc 300
ccctatacat ttggcggcgg caccaagctg gagatcaag 339

<210> SEQ ID NO 14
<211> LENGTH: 113
<212> TYPE: PRT
<213> ORGANISM: Artificial Sequence
<220> FEATURE:
<223> OTHER INFORMATION: Synthetic Artificial Sequence

<400> SEQUENCE: 14

Asp Ile Val Met Thr Gln Ser Pro Ser Ser Leu Ala Val Ser Val Gly
1 5 10 15

Glu Arg Val Thr Ile Ser Cys Lys Ser Ser Gln Ser Leu Leu Asn Ser
20 25 30

Ser Asn Gln Lys Asn Tyr Leu Ala Trp Tyr Gln Gln Lys Pro Gly Gln
35 40 45

Ala Pro Lys Leu Leu Ile Tyr Phe Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

His Tyr Asp Thr Pro Tyr Thr Phe Gly Gly Gly Thr Lys Leu Glu Ile
100 105 110

Lys

```
<210> SEQ ID NO 15
<211> LENGTH: 8
<212> TYPE: PRT
<213> ORGANISM: Artificial Sequence
<220> FEATURE:
<223> OTHER INFORMATION: Synthetic Artificial Sequence

<400> SEQUENCE: 15

Gly Tyr Ser Phe Thr Gly Tyr Thr
1               5


<210> SEQ ID NO 16
<211> LENGTH: 8
<212> TYPE: PRT
<213> ORGANISM: Artificial Sequence
<220> FEATURE:
<223> OTHER INFORMATION: Synthetic Artificial Sequence

<400> SEQUENCE: 16

Ile Asn Pro Tyr Asn Ala Gly Thr
1               5


<210> SEQ ID NO 17
<211> LENGTH: 14
<212> TYPE: PRT
<213> ORGANISM: Artificial Sequence
<220> FEATURE:
<223> OTHER INFORMATION: Synthetic Artificial Sequence

<400> SEQUENCE: 17

Ala Arg Ser Glu Tyr Arg Tyr Gly Gly Asp Tyr Phe Asp Tyr
1               5                   10


<210> SEQ ID NO 18
<211> LENGTH: 12
<212> TYPE: PRT
<213> ORGANISM: Artificial Sequence
<220> FEATURE:
<223> OTHER INFORMATION: Synthetic Artificial Sequence

<400> SEQUENCE: 18

Gln Ser Leu Leu Asn Ser Ser Asn Gln Lys Asn Tyr
1               5                   10


<210> SEQ ID NO 19
<211> LENGTH: 3
<212> TYPE: PRT
<213> ORGANISM: Artificial Sequence
<220> FEATURE:
<223> OTHER INFORMATION: Synthetic Artificial Sequence

<400> SEQUENCE: 19

Phe Ala Ser
1


<210> SEQ ID NO 20
<211> LENGTH: 9
<212> TYPE: PRT
<213> ORGANISM: Artificial Sequence
<220> FEATURE:
<223> OTHER INFORMATION: Synthetic Artificial Sequence

<400> SEQUENCE: 20

Gln Gln His Tyr Asp Thr Pro Tyr Thr
1               5
```

<210> SEQ ID NO 21
<211> LENGTH: 330
<212> TYPE: PRT
<213> ORGANISM: Artificial Sequence
<220> FEATURE:
<223> OTHER INFORMATION: Synthetic Artificial Sequence

<400> SEQUENCE: 21

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 22
<211> LENGTH: 107
<212> TYPE: PRT
<213> ORGANISM: Artificial Sequence
<220> FEATURE:

-continued

```
<223> OTHER INFORMATION: Synthetic Artificial Sequence

<400> SEQUENCE: 22

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

ANTI-CD73 ANTIBODY AND USE THEREOF

SEQUENCE LISTING

This application contains a Sequence Listing which has been submitted electronically in ASCII format and is hereby incorporated by reference in its entirety. Said ASCII copy, created on Nov. 18, 2025, is named "FP220316-Sequence listing-revised" and is 22,000 bytes in size.

TECHNICAL FIELD

The present invention relates to the field of immunology, and in particular to an anti-CD73 antibody and use thereof.

BACKGROUND

Ecto-5'-nucleotidase, namely CD73 protein, is a multi-functional glycoprotein encoded by an NT5E gene and having a protein molecular weight of 70 KD, which is anchored on a cell membrane by glycosylphosphatidylinositol (GPI) (Zimmermann H. *Biochem J.* 1992; 285:345-365).

CD73 is widely distributed on the surface of human tissue cells, and it has been found in research that CD73 is highly expressed in various solid tumors, specifically in cancer cells, dendritic cells, regulatory T cells (Tregs), natural killer cells (NK cells), myeloid-derived suppressor cells (MDSCs), tumor-associated macrophages (TAMs) and the like in a tumor microenvironment. An important feature of the tumor microenvironment is hypoxia. Hypoxia induces the up-regulation of molecules such as hypoxia-inducible factor-1 (HIF-1), thereby leading to the widespread expression of CD73 in the tumor microenvironment (Synnestvedt K, et al. *J Clin Invest.* 2002; 110:993-1002). Analysis of clinical tumor samples shows that high expression of CD73 is a potential biomarker and is closely related to adverse prognosis of various types of tumors, including breast cancer, lung cancer, ovarian cancer, kidney cancer, gastric cancer, head and neck cancer and the like.

CD73 has both hydrolase activity and non-hydrolase activity. The enzyme and non-enzyme functions of CD73 are simultaneously present in the related process of tumor, and mutually promote and maintain the evolution of tumor. More and more studies have found that CD73 is a key regulatory molecule for tumor cell proliferation, metastasis and invasion in vitro, and tumor angiogenesis and tumor immune escape mechanism in vivo, wherein an important immune suppression mechanism is mediated by CD73-adenosine metabolic signal pathway. CD39 at the upstream of CD73 can catalyze ATP to generate adenosine monophosphate (AMP), the generated AMP is converted into adenosine by CD73, and adenosine binds to a downstream adenosine receptor (A2AR). A2AR inhibits a series of signal pathways related to immune activation, such as LCK, MAPK, PKC, and inhibits the immune killing effect of T cells by activating protein kinase A (PKA) and Csk kinase, thereby playing an immune suppression role to enable tumor to achieve immune escape (Antonioli L, et al. *Nat Rev Cancer.* 2013; 13:842-857). Preclinical animal model studies show that CD73 expressed by immune cells and non-immune cells can promote the immune escape, development and metastasis of tumors, wherein the inhibition of cytotoxic T cell (CTL) and NK cell functions by Treg cell-related CD73-adenosine signals is most obvious.

For the treatment of solid tumors, one important aspect to overcome drug resistance and improve the curative effect is to relieve the inhibition effect of the tumor microenvironment (TME) on immune effector cells. TME is a very complex system composed of various cells, intercellular matrix, enzymes, cytokines, metabolites, etc., and it has the characteristics of significant low hydrogen, low pH and high pressure, and is very different from normal tissues. Hypoxia or ATP enrichment caused by chemoradiotherapy for killing tumor cells promotes the cascade reaction of CD39-CD73 adenosine signals, which is beneficial to the proliferation and function of various cancer-promoting cells, and is not beneficial to cancer-inhibiting cells (Regateiro, F. S., Cobbold, S. P. & Waldmann, H. *Clin. Exp. Immunol.* 2013; 171:1-7).

The use of antibodies targeting CD73 or gene knock-out of CD73 in animal models can effectively block the growth and metastasis of tumors. Recently, the use of CD73 monoclonal antibody, small interfering RNA technology, specific inhibitor APCP and the like has achieved remarkable curative effect in anti-tumor treatment of animal experiments, providing a new way for anti-tumor treatment. Evidence from in vivo experiments shows that targeted blockade of CD73 will be an effective treatment means for tumor patients.

The relation between CD73 over-expression and tumor subtype, prognosis and drug response of patients has shown that CD73 can be an important marker for future tumor treatment and detection of individuals. Therefore, the study of the CD73 target is indispensable.

SUMMARY

After intensive studies and creative efforts, the inventor used mammalian cell expression systems to express recombinant human CD73 as an antigen to immunize mice, and obtained hybridoma cells by fusion of mouse spleen cells and myeloma cells. The inventor obtained a hybridoma cell line LT014 (preservation number: CCTCC NO: C2018137) by screening a large number of samples.

The inventor surprisingly has found that the hybridoma cell line LT014 can secrete a specific monoclonal antibody (named as 19F3) specifically binding to human CD73, and the monoclonal antibody can effectively inhibit the enzyme activity reaction of CD73 in a non-substrate competition mode, reduce the production of adenosine, promote the activity of T cells, and exert the effect of inhibiting tumor growth. Further, the inventor has creatively produced humanized antibodies against human CD73 (named as 19F3H1L1, 19F3H2L2 and 19F3H2L3); and on the basis of the above-described humanized antibodies, a novel humanized antibody with ADCC activity eliminated (named as 19F3H1L1(hG1DM), 19F3H2L2(hG1DM) and 19F3H2L3 (hG1DM)) was obtained by introducing an amino acid mutation into the heavy chain constant region.

The inventor has also surprisingly found that the antibodies of the present invention, such as 19F3H1L1, 19F3H2L2 and 19F3H2L3, have the activity of inducing endocytosis of CD73 expressed by cell membranes, and can reduce the activity of CD73, and further mutated antibodies, such as 19F3H2L3(hG1DM), do not bind to FcγRIIIa which causes antibody-mediated cytotoxicity, thereby significantly improving safety. The antibodies of the present invention have potential for use in the treatment of tumors.

One aspect of the present invention relates to an anti-CD73 (for example, human CD73) antibody or an antigen-binding fragment thereof, wherein the anti-CD73 antibody comprises HCDR1, HCDR2 and HCDR2 contained in a heavy chain variable region set forth in SEQ ID NO: 2, SEQ ID NO: 6 or SEQ ID NO: 10; and LCDR1, LCDR2 and LCDR3 contained in a light chain variable region set forth in SEQ ID NO: 4, SEQ ID NO: 8, SEQ ID NO: 12 or SEQ ID NO: 14, preferably, according to an IMGT numbering system, the anti-CD73 antibody comprises:

HCDR1, comprising or consisting of an amino acid sequence set forth in SEQ ID NO: 15, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence, HCDR2, comprising or consisting of an amino acid sequence set forth in SEQ ID NO: 16, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence, HCDR3, comprising or consisting of an amino acid sequence set forth in SEQ ID NO: 17, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence, LCDR1, comprising or consisting of an amino acid sequence set forth in SEQ ID NO: 18, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence, LCDR2, comprising or consisting of an amino acid sequence set forth in SEQ ID NO: 19, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence, and LCDR3, comprising or consisting of an amino acid sequence set forth in SEQ ID NO: 20, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence.

In some embodiments of the present invention, the heavy chain variable region of the antibody comprises or consists of the following sequences:

a sequence set forth in SEQ ID NO: 2, SEQ ID NO: 6 or SEQ ID NO: 10, a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity to the sequence set forth in SEQ ID NO: 2, SEQ ID NO: 6 or SEQ ID NO: 10, or an amino acid sequence having one or more (preferably 1, 2, 3, 4, 5, 6, 7, 8, 9 or 10) conservative amino acid mutations (preferably substitutions, insertions or deletions) compared to the sequence set forth in SEQ ID NO: 2, SEQ ID NO: 6 or SEQ ID NO: 10; and the light chain variable region of the antibody comprises or consists of the following sequences:

a sequence set forth in SEQ ID NO: 4, SEQ ID NO: 8, SEQ ID NO: 12 or SEQ ID NO: 14, a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity to the sequence set forth in SEQ ID NO: 4, SEQ ID NO: 8, SEQ ID NO: 12 or SEQ ID NO: 14, or an amino acid sequence having one or more (preferably 1, 2, 3, 4, 5, 6, 7, 8, 9 or 10) conservative amino acid mutations (preferably substitutions, insertions or deletions) compared to the sequence set forth in SEQ ID NO: 4, SEQ ID NO: 8, SEQ ID NO: 12 or SEQ ID NO: 14.

In some embodiments of the present invention, the heavy chain variable region of the antibody comprises an amino acid sequence set forth in SEQ ID NO: 2, and the light chain variable region of the antibody comprises an amino acid sequence set forth in SEQ ID NO: 4;

the heavy chain variable region of the antibody comprises an amino acid sequence set forth in SEQ ID NO: 6, and the light chain variable region of the antibody comprises an amino acid sequence set forth in SEQ ID NO: 8;

the heavy chain variable region of the antibody comprises an amino acid sequence set forth in SEQ ID NO: 10, and the light chain variable region of the antibody comprises an amino acid sequence set forth in SEQ ID NO: 12; or the heavy chain variable region of the antibody comprises an amino acid sequence set forth in SEQ ID NO: 10, and the light chain variable region of the antibody comprises an amino acid sequence set forth in SEQ ID NO: 14.

In some embodiments of the present invention, the antibody comprises a heavy chain constant region having a sequence set forth in SEQ ID NO: 21, that is, a leucine to alanine point mutation is introduced at position 234 (L234A) and a leucine to alanine point mutation is introduced at position 235 (L235A) based on Ig gamma-1 chain C region and ACCESSION: P01857, and a light chain constant region having a sequence set forth in SEQ ID NO: 22, namely Ig kappa chain C region, ACCESSION: P01834; or the heavy chain constant region is Ig gamma-1 chain C region, ACCESSION: P01857, and the light chain constant region is Ig kappa chain C region, ACCESSION: P01834).

The variable regions of the light chain and the heavy chain determine the binding of the antigen; the variable region of each chain contains three hypervariable regions called complementarity determining regions (CDRs) (CDRs of the heavy chain (H) comprise HCDR1, HCDR2 and HCDR3, and CDRs of the light chain (L) comprise LCDR1, LCDR2 and LCDR3, which are named by Kabat et al., see Bethesda M.d., *Sequences of Proteins of Immunological Interest*, Fifth Edition, NIH Publication 1991; 1-3:91-3242.

Preferably, CDRs may also be defined by the IMGT numbering system, see Ehrenmann, Francois, Quentin Kaas, and Marie-Paule Lefranc. IMGT/3Dstructure-DB and IMGT/DomainGapAlign: a database and a tool for immunoglobulins or antibodies, T cell receptors, MHC, IgSF and MhcSF. *Nucleic acids research* 2009; 38(suppl_1): D301-D307.

The amino acid sequences of the CDR regions of the monoclonal antibody sequences are analyzed according to the IMGT definition by technical means well known to those skilled in the art, for example by using the VBASE2 database.

The antibodies 19F3, 19F3H1L1, 19F3H2L2 and 19F3H2L3 involved in the present invention have identical CDRs.

The amino acid sequences of the 3 CDR regions of the heavy chain variable region are as follows:

```
HCDR1:
                              (SEQ ID NO: 15)
GYSFTGYT,

HCDR2:
                              (SEQ ID NO: 16)
INPYNAGT,
and

HCDR3:
                              (SEQ ID NO: 17)
ARSEYRYGGDYFDY;
```

the amino acid sequences of the 3 CDR regions of the light chain variable region are as follows:

```
LCDR1:
                              (SEQ ID NO: 18)
QSLLNSSNQKNY,

LCDR2:
                              (SEQ ID NO: 19)
FAS,
and

LCDR3:
                              (SEQ ID NO: 20)
QQHYDTPYT.
```

In some embodiments of the present invention, the antibody is a monoclonal antibody.

In some embodiments of the present invention, the antibody is a humanized antibody, a chimeric antibody or a multispecific antibody (e.g., a bispecific antibody).

In some embodiments of the present invention, the antigen-binding fragment is selected from Fab, Fab', $F(ab')_2$, Fd, Fv, dAb, Fab/c, a complementarity determining region fragment, a single chain antibody (e.g., scFv), a humanized antibody, a chimeric antibody and a bispecific antibody.

Another aspect of the present invention relates to an isolated polypeptide selected from the group consisting of:

(1) an isolated polypeptide, comprising sequences set forth in SEQ ID NO: 15, SEQ ID NO: 16 and SEQ ID NO: 17, wherein the polypeptide specifically binds to CD73 as a part of an anti-CD73 antibody, and the antibody further comprises sequences set forth in SEQ ID NO: 18, SEQ ID NO: 19 and SEQ ID NO: 20;

(2) an isolated polypeptide, comprising sequences set forth in SEQ ID NO: 18, SEQ ID NO: 19 and SEQ ID NO: 20, wherein the polypeptide specifically binds to CD73 as a part of an anti-CD73 antibody, and the antibody further comprises sequences set forth in SEQ ID NO: 15, SEQ ID NO: 16 and SEQ ID NO: 17;

(3) an isolated polypeptide, comprising a sequence set forth in SEQ ID NO: 2, SEQ ID NO: 6 or SEQ ID NO: 10, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2, 3, 4, 5, 6, 7, 8, 9 or 10) conservative amino acid mutations (preferably substitutions, insertions or deletions) compared to the sequence, wherein the polypeptide specifically binds to CD73 as a part of an anti-CD73 antibody, and the antibody further correspondingly comprises a sequence set forth in SEQ ID NO: 4, SEQ ID NO: 8 or SEQ ID NO: 12, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2, 3, 4, 5, 6, 7, 8, 9 or 10) conservative amino acid mutations (preferably substitutions, insertions or deletions) compared to the sequence;

(4) an isolated polypeptide, comprising a sequence set forth in SEQ ID NO: 4, SEQ ID NO: 8 or SEQ ID NO: 12, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2, 3, 4, 5, 6, 7, 8, 9 or 10) conservative amino acid mutations (preferably substitutions, insertions or deletions) compared to the sequence, wherein the polypeptide specifically binds to CD73 as a part of an anti-CD73 antibody, and the antibody further correspondingly comprises a sequence set forth in SEQ ID NO: 2, SEQ ID NO: 6 or SEQ ID NO: 10, a sequence having at least 80% to the sequence, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2, 3, 4, 5, 6, 7, 8, 9 or 10) conservative amino acid mutations (preferably substitutions, insertions or deletions) compared to the sequence;

(5) an isolated polypeptide, comprising a sequence set forth in SEQ ID NO: 10, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2, 3, 4, 5, 6, 7, 8, 9 or 10) conservative amino acid mutations (preferably substitutions, insertions or deletions) compared to the sequence, wherein the polypeptide specifically binds to CD73 as a part of an anti-CD73 antibody, and the antibody further correspondingly comprises a sequence set forth in SEQ ID NO: 14, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2, 3, 4, 5, 6, 7, 8, 9 or 10) conservative amino acid mutations (preferably substitutions, insertions or deletions) compared to the sequence; and (6) an isolated polypeptide, comprising a sequence set forth in SEQ ID NO: 14, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2, 3, 4, 5, 6, 7, 8, 9 or 10) conservative amino acid mutations (preferably substitutions, insertions or deletions) compared to the sequence, wherein the polypeptide specifically binds to CD73 as a part of an anti-CD73 antibody, and the antibody further correspondingly comprises a sequence set forth in SEQ ID NO: 10, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2, 3, 4, 5, 6, 7, 8, 9 or 10) conservative amino acid mutations (preferably substitutions, insertions or deletions) compared to the sequence.

Another aspect of the present invention relates to an isolated nucleic acid molecule encoding the antibody or the antigen-binding fragment thereof or the isolated polypeptide according to any one of the aspects of the present invention.

Yet another aspect of the present invention relates to a vector comprising the isolated nucleic acid molecule disclosed herein.

Yet another aspect of the present invention relates to a host cell comprising the isolated nucleic acid molecule or the vector disclosed herein.

Yet another aspect of the present invention relates to a conjugate comprising an antibody and a conjugated moiety, wherein the antibody is the antibody or the antigen-binding fragment thereof according to any one of the aspects of the present invention, and the conjugated moiety is a purification tag (e.g., a His tag), a detectable label; preferably, the conjugated moiety is a radioisotope, a fluorescent substance, a chemiluminescent substance, a colored substance, polyethylene glycol or an enzyme.

Yet another aspect of the present invention relates to a fusion protein or a multispecific antibody (preferably a bispecific antibody) comprising the antibody or the antigen-binding fragment thereof according to any one of the aspects of the present invention.

Yet another aspect of the present invention relates to a kit comprising the antibody or the antigen-binding fragment thereof according to any one of the aspects of the present invention, the conjugate, the fusion protein or the multispecific antibody of the present invention; preferably, the kit further comprises a secondary antibody specifically recognizing the antibody; optionally, the secondary antibody further comprises a detectable label, such as a radioisotope, a fluorescent substance, a chemiluminescent substance, a colored substance or an enzyme.

Yet another aspect of the present invention relates to use of the antibody or the antigen-binding fragment thereof according to any one of the aspects of the present invention, the conjugate, the fusion protein or the multispecific antibody of the present invention in preparing a kit used for detecting the presence or level of CD73 in a sample.

Yet another aspect of the present invention relates to a pharmaceutical composition comprising the antibody or the antigen-binding fragment thereof according to any one of the aspects of the present invention, the conjugate, the fusion protein or the multispecific antibody of the present invention; optionally, the pharmaceutical composition further comprises a pharmaceutically acceptable carrier and/or excipient. Preferably, the pharmaceutical composition is in a form suitable for administration by subcutaneous injection, intradermal injection, intravenous injection, intramuscular injection or intralesional injection.

Yet another aspect of the present invention relates to use of the antibody or the antigen-binding fragment thereof according to any one of the aspects of the present invention, the conjugate, the fusion protein or the multispecific antibody of the present invention in preparing drugs for treating and/or preventing a tumor (such as a solid tumor, preferably non-small cell lung cancer, prostate cancer (including metastatic castration-resistant prostate cancer (mCRPC)), triple-negative breast cancer, ovarian cancer, colorectal cancer (including colorectal cancer microsatellite stability (MSS)), gastric cancer, melanoma, head and neck cancer, renal cell carcinoma or pancreatic ductal adenocarcinoma), or in preparing a drug for diagnosing a tumor.

Yet another aspect of the present invention relates to a hybridoma cell line LT014, which was deposited at China Center for Type Culture Collection (CCTCC) with a collection number of CCTCC NO: C2018137.

In the present invention, unless otherwise specified, the scientific and technical terms used herein have the meanings generally understood by those skilled in the art. In addition, the laboratory operations of cell culture, molecular genetics, nucleic acid chemistry and immunology used herein are the routine procedures widely used in the corresponding fields. Meanwhile, in order to better understand the present invention, the definitions and explanations of the relevant terms are provided below.

As used herein, the term $EC_{50}$ refers to the concentration for 50% of maximal effect, i.e., the concentration that can cause 50% of the maximal effect.

As used herein, the term "antibody" refers to an immunoglobulin molecule that generally consists of two pairs of polypeptide chains (each pair with one "light" (L) chain and one "heavy" (H) chain). Antibody light chains are classified as κ and λ light chains. Heavy chains are classified as μ, δ, γ, α, or ε. Isotypes of antibodies are defined as IgM, IgD, IgG, IgA, and IgE. In light chains and heavy chains, the variable region and constant region are linked by a "J" region of about 12 or more amino acids, and the heavy chain also comprises a "D" region of about 3 or more amino acids. Each heavy chain consists of a heavy chain variable region ($V_H$) and a heavy chain constant region (CH). The heavy chain constant region consists of 3 domains ($C_{H1}$, $C_{H2}$, and $C_{H3}$). Each light chain consists of a light chain variable region ($V_L$) and a light chain constant region ($C_L$). The light chain constant region consists of one domain $C_L$. The constant region of the antibody can mediate the binding of immunoglobulins to host tissues or factors, including various cells of the immune system (e.g., effector cells) and the first component (C1q) of the classical complement system. The $V_H$ and $V_L$ regions can be further subdivided into highly variable regions (called complementarity determining regions (CDRs)), between which conservative regions called framework regions (FRs) are distributed. Each $V_H$ and $V_L$ consists of 3 CDRs and 4 FRs arranged from amino terminus to carboxyl terminus in the following order: FR1, CDR1, FR2, CDR2, FR3, CDR3, FR4. The variable regions ($V_H$ and $V_L$) of each heavy chain/light chain pair form antigen-binding sites, respectively. The assignment of amino acids to the regions or domains is based on Kabat Sequences of Proteins of Immunological Interest (National Institutes of Health, Bethesda, M.d. (1987 and 1991)), or Chothia & Lesk *J. Mol. Biol.* 1987; 196:901-917; Chothia et al. Nature 1989; 342:878-883 or the definition of the IMGT numbering system, see the definition in Ehrenmann, Francois, Quentin Kaas, and Marie-Paule Lefranc. IMGT/3Dstructure-DB and IMGT/DomainGapAlign: a database and a tool for immunoglobulins or antibodies, T cell receptors, MHC, IgSF and MhcSF. *Nucleic acids research* 2009; 38(suppl_1): D301-D307. The term "antibody" is not limited by any specific method for producing antibody. For example, the antibody includes, in particular, a recombinant antibody, a monoclonal antibody, and a polyclonal antibody. The antibody may be antibodies of different isotypes, such as IgG (e.g., subtype IgG1, IgG2, IgG3 or IgG4), IgA1, IgA2, IgD, IgE or IgM.

As used herein, the terms "mAb" and "monoclonal antibody" refer to an antibody or a fragment of an antibody that is derived from a group of highly homologous antibodies, i.e., from a group of identical antibody molecules, except for natural mutations that may occur spontaneously. The monoclonal antibody is highly specific for a single epitope on an antigen. The polyclonal antibody, relative to the monoclonal antibody, generally comprises at least 2 or more different antibodies which generally recognize different epitopes on an antigen. Monoclonal antibodies can generally be obtained using hybridoma technology first reported by Kohler et al (Köhler G, Milstein C. Continuous cultures of fused cells secreting antibody of predefined specificity [J]. *Nature*, 1975; 256(5517): 495), but can also be obtained using recombinant DNA technology (see, e.g., U.S. Pat. No. 4,816,567).

As used herein, the term "humanized antibody" refers to an antibody or an antibody fragment obtained when all or a part of CDR regions of a human immunoglobulin (receptor antibody) are replaced by the CDR regions of a non-human antibody (donor antibody), wherein the donor antibody may be a non-human (e.g., mouse, rat or rabbit) antibody having expected specificity, affinity or reactivity. In addition, some amino acid residues in the framework regions (FRs) of the receptor antibody can also be replaced by the amino acid residues of corresponding non-human antibodies or by the amino acid residues of other antibodies to further improve or optimize the performance of the antibody. For more details on humanized antibodies, see, e.g., Jones et al., *Nature* 1986; 321:522-525; Reichmann et al., Nature 1988; 332:323-329; Presta, *Curr. Op. Struct. Biol.*, 1992; 2:593-596; and Clark M. Antibody humanization: a case of the 'Emperor's new clothes'? [J]. *Immunol. Today*, 2000; 21(8): 397-402.

As used herein, the term "isolated" refers to obtaining by artificial means from natural state. If a certain "isolated" substance or component appears in nature, it may be the case that change occurs in its natural environment, or that it is isolated from the natural environment, or both. For example, a certain non-isolated polynucleotide or polypeptide naturally occurs in a certain living animal, and the same polynucleotide or polypeptide with high purity isolated in such a natural state is referred to as an isolated polynucleotide or polypeptide. The term "isolated" does not exclude the existence of artificial or synthetic substances or other impurities that do not affect the activity of the substance.

As used herein, the term "vector" refers to a nucleic acid vehicle into which a polynucleotide can be inserted. When a vector allows for the expression of the protein encoded by the inserted polynucleotide, the vector is referred to as an expression vector. The vector can be introduced into a host cell by transformation, transduction, or transfection so that the genetic substance elements carried by the vector can be expressed in the host cell. Vectors are well known to those skilled in the art, including but not limited to: plasmids; phagemids; cosmids; artificial chromosomes, such as yeast artificial chromosome (YAC), bacterial artificial chromosome (BAC), or P1-derived artificial chromosome (PAC); phages such as lambda phages or M13 phages; and animal viruses. Animal viruses that can be used as vectors include, but are not limited to retroviruses (including lentiviruses), adenoviruses, adeno-associated viruses, herpes viruses (such as herpes simplex virus), poxviruses, baculoviruses, papillomaviruses, and papovaviruses (such as SV40). A vector may comprise a variety of elements that control expression, including, but not limited to promoter sequences, transcription initiation sequences, enhancer sequences, selection elements, and reporter genes. In addition, the vector may further comprise a replication initiation site.

As used herein, the term "host cell" refers to cells to which vectors can be introduced, including, but not limited to, prokaryotic cells such as *E. coli* or *Bacillus subtilis*, fungal cells such as yeast cells or *aspergillus*, insect cells such as S2 drosophila cells or Sf9, or animal cells such as fibroblasts, CHO cells, COS cells, NSO cells, HeLa cells, GS cells, BHK cells, HEK 293 cells, or human cells.

As used herein, the term "specific binding" refers to a non-random binding reaction between two molecules, such as a reaction between an antibody and an antigen it targets. In some embodiments, an antibody specifically binding to an antigen (or an antibody specific to an antigen) means that the antibody binds to the antigen with an affinity ($K_D$) of less than about $10^{-5}$ M, e.g., less than about $10^{-6}$ M, $10^{-7}$ M, $10^{-8}$M, $10^{-9}$M or $10^{-10}$ M or less.

As used herein, the term "$K_D$" refers to a dissociation equilibrium constant for a specific antibody-antigen interaction, which is used to describe the binding affinity between the antibody and the antigen. A smaller dissociation equilibrium constant indicates a stronger antibody-antigen binding and a higher affinity between the antibody and the antigen. Generally, antibodies bind to antigens (e.g., PD-1 protein) with a dissociation equilibrium constant ($K_D$) of less than about $10^{-5}$ M, e.g., less than about $10^{-6}$ M, $10^{-7}$ M, $10^{-8}$ M, $10^{-9}$ M or $10^{-10}$ M or less. $K_D$ can be determined using methods known to those skilled in the art, e.g., using a Fortebio system.

As used herein, the terms "monoclonal antibody" and "mAb" have the same meaning and can be used interchangeably; the terms "polyclonal antibody" and "pAb" have the same meaning and can be used interchangeably; the terms "polypeptide" and "protein" have the same meaning and can be used interchangeably. Besides, herein, amino acids are generally represented by single-letter and three-letter abbreviations known in the art. For example, alanine can be represented by A or Ala.

As used herein, the term "pharmaceutically acceptable carrier and/or excipient" refers to a carrier and/or excipient that is pharmacologically and/or physiologically compatible with the subject and the active ingredient. Such carriers and/or excipients are well known in the art (see, e.g., Remington's Pharmaceutical Sciences, edited by Gennaro A R, 19th Ed., Pennsylvania: Mack Publishing Company, 1995), including, but not limited to: pH regulators, surfactants, adjuvants, and ionic strength enhancers. For example, the pH regulators include, but are not limited to, phosphate buffer; the surfactants include, but are not limited to, cationic, anionic, or non-ionic surfactants, such as Tween-80; the ionic strength enhancers include, but are not limited to, sodium chloride.

As used herein, the term "effective amount" refers to an amount sufficient to obtain or at least partially obtain desired effects. For example, a prophylactically effective amount against a disease (e.g., a tumor) refers to an amount sufficient to prevent, stop, or delay the onset of a disease (e.g., a tumor); a therapeutically effective amount refers to an amount sufficient to cure or at least partially stop a disease and complications thereof in patients suffering from the disease.

Beneficial Effects of the Present Invention the monoclonal antibody of the present invention can specifically bind to CD73 well, and can effectively inhibit the enzyme activity reaction of CD73 in a non-substrate competition mode, reduce the production of adenosine, and promote the activity of T cells and the tumor inhibitory effect.

Notes on the Deposit of Biological Materials:

the hybridoma cell line LT014 (also called CD73-19F3) was deposited at China Center for Type Culture Collection (CCTCC) on Jun. 21, 2018 with a collection number of CCTCC NO: C2018137 and a collection address of Wuhan University, Wuhan, China, postal code: 430072.

DETAILED DESCRIPTION

Figure 1:
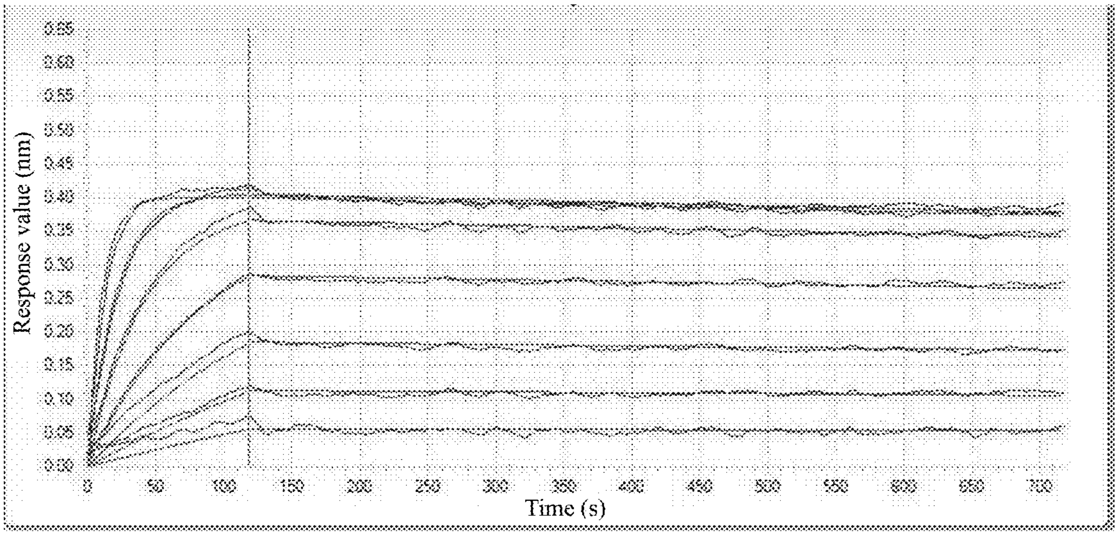
FIG. 1. Detection results of affinity constants of 19F3H2L3 for HNT5E(1-552)-his. The antibody concentrations for the curve pairs from top to bottom are 200 nM, 100 nM, 50 nM, 25 nM, 12.5 nM, 6.25 nM and 3.125 nM, respectively.

The embodiments of the present invention will be described in detail below with reference to the examples. Those skilled in the art will understand that the following examples are only for illustrating the present invention, and should not be construed as limitations on the scope of the present invention. In the cases where the techniques or conditions are not specified, the examples were implemented according to the techniques or conditions described in the literature in the art (e.g., see, *Molecular Cloning: A Laboratory Manual*, authored by J. Sambrook et al., and translated by Peitang Huang et al., $3^{rd}$ Edition, Science Press) or according to the product manual. Reagents or instruments used are commercially available conventional products if the manufacturers thereof are not specified. For example, MDA-MB-231 cells and U87-MG cells can be purchased from ATCC.

In the following examples of the present invention, BALB/c mice used were purchased from Guangdong Medical Experimental Animal Center.

In the following examples of the present invention, the positive control antibody MEDI9447 (oleclumab) used was produced by Akeso Biopharma Co. Ltd., the sequence of which is as same as the antibody SEQ ID NOs: 21-24 described in the Medlmmune Limited published patent with the publication number: US20160129108A1.

In the following examples of the present invention, AD2 used was purchased from Biolegend (Cat. No. 344002).

Example 1. Preparation of Anti-CD73 Antibody 19F3

1. Preparation of Hybridoma Cell Line LT014

The antigen used to prepare the anti-CD73 antibody was human NT5E-His (for NT5E, GenbankID: NP_002517.1, position: 1-552). Spleen cells of immunized mice were taken to fuse with myeloma cells of the mice to prepare hybridoma cells. Hybridoma cells were screened by indirect ELISA using human NT5E-Biotin (for NT5E, GenbankID: NP 002517.1, position: 1-552) as an antigen, and hybridoma cells capable of secreting an antibody specifically binding to CD73 were obtained. The hybridoma cells obtained by screening were subjected to limiting dilution to obtain a stable hybridoma cell line. The hybridoma cell line was named as hybridoma cell line LT014, and the monoclonal antibody secreted therefrom was named as 19F3.

The hybridoma cell line LT014 (also called CD73-19F3) was deposited at China Center for Type Culture Collection (CCTCC) on Jun. 21, 2018, with a collection number of CCTCC NO: C2018137 and a collection address of Wuhan University, Wuhan, China, postal code: 430072. All restrictions upon public access to the deposited material will be irrevocably removed upon the grant of a patent on this application.

2. Preparation of Anti-CD73 Antibody 19F3

The LT014 cell line prepared above was cultured with a chemical defined medium (CD medium, containing 1% Penicillin-Streptomycin) in a 5% $CO_2$ cell incubator at 37° C. After 7 days, the cell culture supernatant was collected, subjected to high-speed centrifugation and vacuum filtration through a microfiltration membrane, and purified by using a HiTrap protein A HP column to obtain an antibody 19F3.

Example 2. Sequence Analysis of Anti-CD73 Antibody 19F3 mRNA was extracted from the cell line LT014 cultured in Example 1 according to the method described in the manual of RNAprep pure Cell/Bacteria Kit (Tiangen, Cat. No. DP430).

cDNA was synthesized according to the manual of Invitrogen SuperScript® III First-Strand Synthesis System for RT-PCR and amplified by PCR.

The PCR-amplified products were directly subjected to TA cloning according to the manual of the pEASY-T1 Cloning Kit (Transgen CT101).

The product obtained by performing TA cloning of the antibody 19F3 against CD73 on the LT014 cell line was directly sequenced. The sequencing results are as follows.

The nucleotide sequence of the heavy chain variable region is set forth in SEQ ID NO: 1 with a length of 363 bp.

The encoded amino acid sequence is set forth in SEQ ID NO: 2 with a length of 121 aa;

wherein the sequence of the heavy chain CDR1 is set forth in SEQ ID NO: 15, the sequence of the heavy chain CDR2 is set forth in SEQ ID NO: 16, and the sequence of the heavy chain CDR3 is set forth in SEQ ID NO: 17.

The nucleotide sequence of the light chain variable region is set forth in SEQ ID NO: 3 with a length of 339 bp.

The encoded amino acid sequence is set forth in SEQ ID NO: 4 with a length of 113 aa;

wherein the sequence of the light chain CDR1 is set forth in SEQ ID NO: 18, the sequence of the light chain CDR2 is set forth in SEQ ID NO: 19, and the sequence of the light chain CDR3 is set forth in SEQ ID NO: 20.

Example 3. Design and Preparation of Light and Heavy Chains of Humanized Anti-Human CD73 Antibodies 1. Design of Light and Heavy Chains of Humanized Anti-Human CD73 Antibodies 19F3H1L1, 19F3H2L2 and 19F3H2L3

Based on the three-dimensional crystal structure of human CD73 protein (Hage T, Reinemer P, Sebald W., Crystals of a 1:1 Complex Between Human Interleukin-4 and the Extracellular Domain of Its Receptor Alpha Chain, *Eur. J. Biochem.,* 1998; 258 (2): 831-6.) and the sequence of antibody 19F3 obtained in Example 2, the variable region sequences of antibodies 19F3H1L1, 19F3H2L2 and 19F3H2L3 were obtained by computer modeling and mutation design (antibody constant region sequences from NCBI database: the heavy chain constant region is Ig gamma-1 chain C region, ACCESSION: P01857 (SEQ ID NO: 23); the light chain constant region is Ig kappa chain C region, ACCESSION: P01834 (SEQ ID NO: 24)).

The designed variable region sequences are as follows:

(1) Sequences of heavy and light chain variable regions of humanized monoclonal antibody 19F3H1L1

The nucleotide sequence of the heavy chain variable region is set forth in SEQ ID NO: 5 with a length of 363 bp.

The encoded amino acid sequence is set forth in SEQ ID NO: 6 with a length of 121 aa, wherein the sequence of the heavy chain CDR1 is set forth in SEQ ID NO: 15, the sequence of the heavy chain CDR2 is set forth in SEQ ID NO: 16, and the sequence of the heavy chain CDR3 is set forth in SEQ ID NO: 17.

The nucleotide sequence of the light chain variable region is set forth in SEQ ID NO: 7 with a length of 339 bp.

The encoded amino acid sequence is set forth in SEQ ID NO: 8 with a length of 113 aa, wherein the sequence of the light chain CDR1 is set forth in SEQ ID NO: 18, the sequence of the light chain CDR2 is set forth in SEQ ID NO: 19, and the sequence of the light chain CDR3 is set forth in SEQ ID NO: 20.

(2) Sequences of heavy and light chain variable regions of humanized monoclonal antibody 19F3H2L2

The nucleotide sequence of the heavy chain variable region is set forth in SEQ ID NO: 9 with a length of 363 bp.

The encoded amino acid sequence is set forth in SEQ ID NO: 10 with a length of 121 aa, wherein the sequence of the heavy chain CDR1 is set forth in SEQ ID NO: 15, the sequence of the heavy chain CDR2 is set forth in SEQ ID NO: 16, and the sequence of the heavy chain CDR3 is set forth in SEQ ID NO: 17.

The nucleotide sequence of the light chain variable region is set forth in SEQ ID NO: 11 with a length of 339 bp.

The encoded amino acid sequence is set forth in SEQ ID NO: 12 with a length of 113 aa, wherein the sequence of the light chain CDR1 is set forth in SEQ ID NO: 18, the sequence of the light chain CDR2 is set forth in SEQ ID NO: 19, and the sequence of the light chain CDR3 is set forth in SEQ ID NO: 20.

(3) Sequences of heavy and light chain variable regions of humanized monoclonal antibody 19F3H2L3

The nucleotide sequence of the heavy chain variable region is set forth in SEQ ID NO: 9 with a length of 363 bp.

The encoded amino acid sequence is set forth in SEQ ID NO: 10 with a length of 121 aa, wherein the sequence of the heavy chain CDR1 is set forth in SEQ ID NO: 15, the sequence of the heavy chain CDR2 is set forth in SEQ ID NO: 16, and the sequence of the heavy chain CDR3 is set forth in SEQ ID NO: 17.

The nucleotide sequence of the light chain variable region is set forth in SEQ ID NO: 13 with a length of 339 bp.

The encoded amino acid sequence is set forth in SEQ ID NO: 14 with a length of 113 aa, wherein the sequence of the light chain CDR1 is set forth in SEQ ID NO: 18, the sequence of the light chain CDR2 is set forth in SEQ ID NO: 19, and the sequence of the light chain CDR3 is set forth in SEQ ID NO: 20.

2. Preparation of Humanized Antibodies 19F3H1L1, 19F3H2L2 and 19F3H2L3

The heavy chain constant regions were all Ig gamma-1 chain C region, ACCESSION: P01857; and the light chain constant regions were all Ig kappa chain C region, ACCESSION: P01834.

The heavy chain cDNA and light chain cDNA of 19F3H1L1, the heavy chain cDNA and light chain cDNA of 19F3H2L2 and the heavy chain cDNA and light chain cDNA of 19F3H2L3 were respectively cloned into pUC57simple (provided by GenScript) vectors to obtain pUC57simple-19F3H1, pUC57simple-19F3L1, pUC57simple-19F3H2, pUC57simple-19F3L2 and pUC57simple-19F3L3, respectively. Referring to the standard technique introduced in *Molecular Cloning Laboratory Manual* (*Second Edition*), the heavy and light chain full-length genes synthesized by EcoRI&HindIII digestion were subcloned into an expression vector pcDNA3.1 by an restriction enzyme (EcoRI&HindIII) through digestion to obtain expression plasmids pcDNA3.1-19F3H1, pcDNA3.1-19F3L1, pcDNA3.1-19F3H2, pcDNA3.1-19F3L2 and pcDNA3.1-19F3L3, and the heavy/light chain genes of the recombinant expression plasmids were further subjected to sequencing analysis. Then the designed gene combinations comprising corresponding light and heavy chain recombinant plasmids (pcDNA3.1-19F3H1/pcDNA3.1-19F3L1, pcDNA3.1-19F3H2/pcDNA3.1-19F3L2 and pcDNA3.1-19F3H2/pcDNA3.1-19F3L3) were respectively co-transfected into 293F cells, and the culture solutions were collected and purified. After the sequences were verified, endotoxin-free expression plasmids were prepared, and were transiently transfected into HEK293 cells for antibody expression. The culture solutions were collected after 7 days, and subjected to affinity purification on a Protein A column to obtain humanized antibodies.

3. Preparation of Humanized Antibodies 19F3H1L1 (hG1DM), 19F3H2L2(hG1DM) and 19F3H2L3(hG1DM)

The light chain constant regions of the antibodies 19F3H1L1(hG1DM), 19F3H2L2(hG1DM) and 19F3H2L3 (hG1DM) are the Ig kappa chain C region, ACCESSION: P01834, see SEQ ID NO: 22.

On the basis of Ig gamma-1 chain C region, ACCESSION: P01857, humanized antibodies were obtained by introducing a leucine-to-alanine point mutation at position 234 (L234A) and a leucine-to-alanine point mutation at position 235 (L235A) in the heavy chain constant region, see SEQ ID NO: 21, and were designated as 19F3H1L1 (hG1DM), 19F3H2L2(hG1DM) and 19F3H2L3(hG1DM), respectively.

The heavy chain cDNA and light chain cDNA of 19F3H1L1(hG1DM), the heavy chain cDNA and light chain cDNA of 19F3H2L2(hG1DM) and the heavy chain cDNA and light chain cDNA of 19F3H2L3(hG1DM) were respectively cloned into pUC57simple (provided by Genscript) vectors to obtain pUC57simple-19F3H1(hG1DM), pUC57simple-19F3L1, pUC57simple-19F3H2(hG1DM), pUC57simple-19F3L2 and pUC57simple-19F3L3, respectively. Referring to the standard techniques described in *Molecular Cloning: A Laboratory Manual* (*Second Edition*), the heavy and light chain full-length genes synthesized by EcoRI&HindIII digestion were subcloned into an expression vector pcDNA3.1 by an restriction enzyme (EcoRI&HindIII) through digestion to obtain expression plasmids pcDNA3.1-19F3H1(hG1DM), pcDNA3.1-19F3L1, pcDNA3.1-19F3H2(hG1DM), pcDNA3.1-19F3L2 an pcDNA3.1-19F3L3, and the heavy/light chain genes of the recombinant expression plasmids were further subjected to sequencing analysis. Then the designed gene combinations comprising corresponding light and heavy chain recombinant plasmids (pcDNA3.1-19F3H1(hG1DM)/pcDNA3.1-19F3L1, pcDNA3.1-19F3H2(hG1DM)/pcDNA3.1-19F3L2 and pcDNA3.1-19F3H2(hG1DM)/pcDNA3.1-19F3L3) were respectively co-transfected into 293F cells, and the culture solutions were collected and purified. After the sequences were verified, endotoxin-free expression plasmids were prepared, and were transiently transfected into HEK293 cells for antibody expression. The culture solutions were collected after 7 days, and subjected to affinity purification on a Protein A column to obtain humanized antibodies.

Example 4. Determination of Binding Activity of Anti-CD73 Antibody to Antigen Human NT5E-Biotin by ELISA Experimental steps: a microplate was coated with streptavidin at 2 μg/mL, and then the microplate was incubated at 4° C. for 12 hours. The antigen-coated microplate was rinsed for once with PBST after incubation, and then blocked with a PBST solution containing 1% BSA as a microplate blocking solution for 2 hours. After blocking, the microplate was washed 3 times with PBST. Then, 0.5 μg/mL antigen human NT5E-Biotin was added, and the plate was washed 3 times with PBST after incubated at 37° C. for 30 minutes. The antibody serially diluted with the PBST solution was added to the wells of the microplate. The antibody dilution gradients are shown in Table 1. The microplate containing the test antibodies was incubated at 37° C. for 30 minutes, and then washed 3 times with PBST. After the plate was washed, the secondary antibody working solution of HRP-labeled goat anti-human IgG (H+L) (Jackson, Cat. No. 109-035-088) diluted in a ratio of 1:5000 or HRP-labeled goat anti-mouse IgG (H+L) (Jackson, Cat. No. 115-035-062) diluted in a ratio of 1:5000 was added, and then the plate was incubated at 37° C. for 30 minutes. After incubation, the plate was washed 4 times with PBST, TMB (Neogen, 308177) was added in the dark for color development for 5 min, and then a stop solution was added to terminate chromogenic reaction. The microplate was put into a microplate reader immediately, and the OD value of each well in the microplate was read at the light wavelength of 450 nm. The data were analyzed by SoftMax Pro 6.2.1.

OD values of doses for detecting the binding of anti-CD73 antibody to the antigen human NT5E-Biotin are shown in Table 1. The binding $EC_{50}$ of the antibody was calculated by curve fitting using antibody concentration as the abscissa and absorbance value as the ordinate, and the results are shown in Table 1 below.

Experimental results show that the antibodies 19F3 H1L1, 19F3 H2L2 and 19F3 H2L3 and the murine antibody 19F3 can effectively bind to human NTSE-Biotin, and the binding efficiency is in a dose-dependent relationship. Under the basically same experimental conditions, $EC_{50}$ of 19F3 H1L1 binding to human NTSE-Biotin was 0.049 nM, $EC_{50}$ of 19F3 H2L2 binding to human NTSE-Biotin was 0.064 nM, $EC_{50}$ of 19F3 H2L3 binding to human NTSE-Biotin was 0.061 nM, $EC_{50}$ of the positive drug MEDI9447 for the same target binding to human NTSE-Biotin was 0.048 nM, and $EC_{50}$ of murine antibody 19F3 binding to human NTSE-Biotin was 0.018 nM.

The above experimental results show that the binding activity of 19F3 H1L1, 19F3 H2L2, 19F3 H2L3 and murine antibody 19F3 to human NTSE-Biotin respectively is comparable to that of the positive drug MEDI9447 for the same target under the same experimental conditions, indicating that 19F3 H1L1, 19F3 H2L2 and 19F3 H2L3 have the function of effectively binding to CD73.

TABLE 1

Detection results of binding activity of 19F3H1L1, 19F3H2L2, 19F3H2L3 and murine antibody 19F3 to HNT5E-Biotin

| Antibody dilution | Antigen coating: SA (2 μg/mL) Human NT5E-Biotin (0.5 μg/mL) | | | | | | | | | |
|---|---|---|---|---|---|---|---|---|---|---|
| (μg/mL) | 19F3 H1L1 | | 19F3 H2L2 | | 19F3 H2L3 | | MEDI9447 | | 19F3 | |
| 0.333 | 2.648 | 2.640 | 2.598 | 2.688 | 2.623 | 2.588 | 2.548 | 2.527 | 2.706 | 2.743 |
| 1:3 | 2.601 | 2.697 | 2.578 | 2.618 | 2.581 | 2.582 | 2.573 | 2.604 | 2.736 | 2.763 |
| 1:9 | 2.407 | 2.332 | 2.163 | 2.330 | 2.186 | 2.257 | 2.268 | 2.284 | 2.566 | 2.641 |
| 1:27 | 1.821 | 1.820 | 1.579 | 1.680 | 1.626 | 1.649 | 1.774 | 1.742 | 2.330 | 2.361 |
| 1:81 | 1.044 | 1.035 | 0.870 | 0.933 | 0.918 | 0.931 | 1.058 | 1.030 | 1.693 | 1.769 |
| 1:243 | 0.525 | 0.516 | 0.434 | 0.454 | 0.450 | 0.457 | 0.536 | 0.528 | 1.001 | 1.000 |
| 1:729 | 0.260 | 0.273 | 0.239 | 0.247 | 0.241 | 0.252 | 0.272 | 0.275 | 0.446 | 0.470 |
| 0 | 0.125 | 0.123 | 0.119 | 0.123 | 0.120 | 0.123 | 0.121 | 0.116 | 0.060 | 0.062 |
| Secondary antibody | HRP-labeled goat anti-human IgG (H + L) (1:5000) | | | | | | | | HRP-labeled goat anti-mouse IgG (H + L) (1:5000) | |
| $EC_{50}$ (nM) | 0.049 | | 0.064 | | 0.061 | | 0.048 | | 0.018 | |

Example 5. Kinetic Parameters for Binding of Humanized Antibodies 19F3H2L3, 19F3H2L2 and MEDI9447 to the Antigen Human HNT5E (1-552)-his Determined Using Fortebio Molecular Interaction Instrument The sample dilution buffer was PBST, pH 7.4. 5 μg/mL antibody was immobilized at on the Protein A sensor for 15 s. The sensor was equilibrated in the buffer for 120 s. The binding of the immobilized antibody on the sensor to the antigen human NT5E(1-552)-his at concentrations of 3.125-200 nM (two-fold dilution) was determined for 120 s. The antigen-antibody was dissociated in the buffer for 600 s. The sensor was refreshed with 10 mM glycine solution (pH 1.5). The detection temperature was 37° C., the detection frequency was 0.6 Hz, and the sample plate shaking rate was 1000 rpm. The data were analyzed by 1:1 model fitting to obtain affinity constants.

Figure 2:
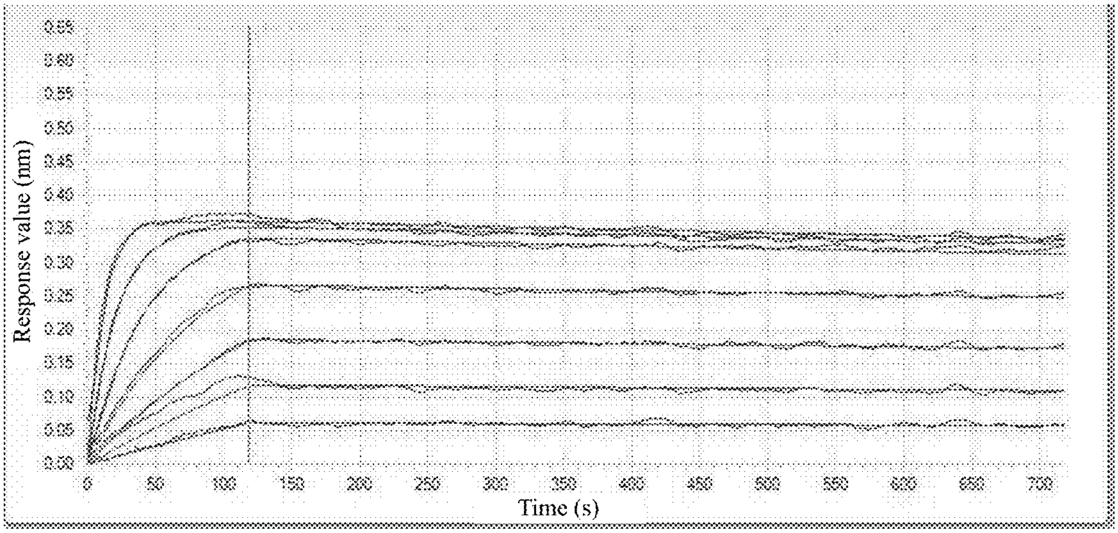
FIG. 2. Detection results of affinity constants of 19F3H2L2 for HNT5E(1-552)-his. The antibody concentrations for the curve pairs from top to bottom are 200 nM, 100 nM, 50 nM, 25 nM, 12.5 nM, 6.25 nM and 3.125 nM, respectively.
Figure 3:
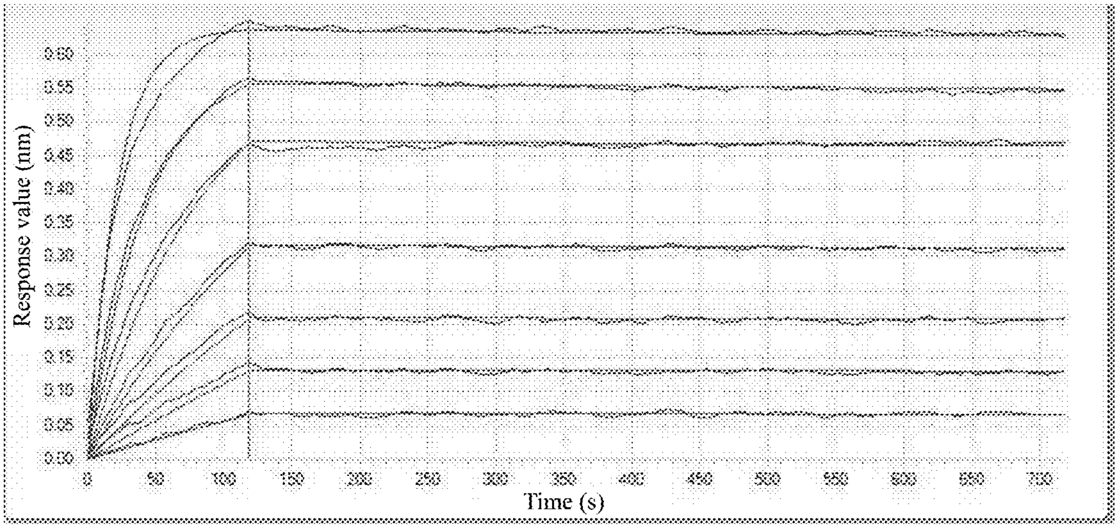
FIG. 3. Detection results of affinity constants of MEDI9447 for HNT5E(1-552)-his. The antibody concentrations for the curve pairs from top to bottom are 200 nM, 100 nM, 50 nM, 25 nM, 12.5 nM, 6.25 nM and 3.125 nM, respectively.

The results of measuring the affinity constants of humanized antibodies 19F3H2L3, 19F3H2L2 and MEDI9447 (as control antibodies) and human CD73 are shown in Table 2, and the detection results are shown in FIGS. 1-3.

As shown in Table 2 and FIGS. 1-3, the affinity constants of humanized antibodies 19F3H2L3, 19F3H2L2 and MEDI9447 and human CD73 were 1.04E-10 M, 2.36E-10 M, 2.59E-10 M and 1.04E-10 M sequentially.

The above experimental results show that the binding ability of 19F3H2L3 and 19F3H2L2 to HNT5E(1-552)-his is comparable, indicating that the humanized antibodies 19F3H2L3 and 19F3H2L2 have strong binding capacity to human CD73.

TABLE 2

Determination of affinity constants of 19F3H2L3, 19F3H2L2 and HNT5E(1-552)-his

| Test antibodies | KD (M) | kon (1/Ms) | S E (kon) | kdis (1/s) | S E (kdis) | Rmax (nm) |
|---|---|---|---|---|---|---|
| 19F3 H2L3 | 2.36E−10 | 4.82E+05 | 7.74E+03 | 1.14E−04 | 5.87E−06 | 0.34-0.41 |
| 19F3 H2L2 | 2.59E−10 | 4.80E+05 | 6.44E+03 | 1.24E−04 | 4.86E−06 | 0.35-0.39 |
| MEDI9447 | 1.04E−10 | 2.34E+05 | 3.20E+03 | 2.44E−05 | 5.02E−06 | 0.59-0.82 |

$K_D$ is the affinity constant;
$K_D$ = kdis/kon

Example 6. Binding Ability of 19F3H2L3 Antibody Determined by FACS

MDA-MB-231 cells in logarithmic phase were digested with conventional trypsin, centrifuged, and resuspended in PBSA. The cells were filled into 1.5 mL centrifuge tubes (0.3 million cells in each tube) and centrifuged at 5600 rpm for 5 min to remove the supernatant. 100 μL of CD73 antibodies diluted by PBSA with the final concentrations of 100 nM, 33.33 nM, 11.11 nM, 3.7 nM, 1.23 nM, 0.41 nM, 0.14 nM and 0.05 nM were added, respectively. The system was mixed gently and uniformly, and then was incubated on ice for 1 h. Then 500 μL of PBSA was added, and the mixture was centrifuged at 5600 rpm for 5 min to remove the supernatant. The 500-fold diluted FITC labeled goat anti-human IgG secondary antibody (Jackson, Cat. No. 109-095-098) was added to resuspend cell precipitates, and the mixture was incubated on ice in the dark for 0.5 h. 500 μL of PBSA was added, and the mixture was centrifuged at 5600 rpm for 5 min to remove the supernatant. At last, 200 μL of PBSA was added to resuspend cell precipitates, and the mixture was transferred to a flow tube for detection by a flow cytometer (BD FACSCalibur™).

Figure 4:
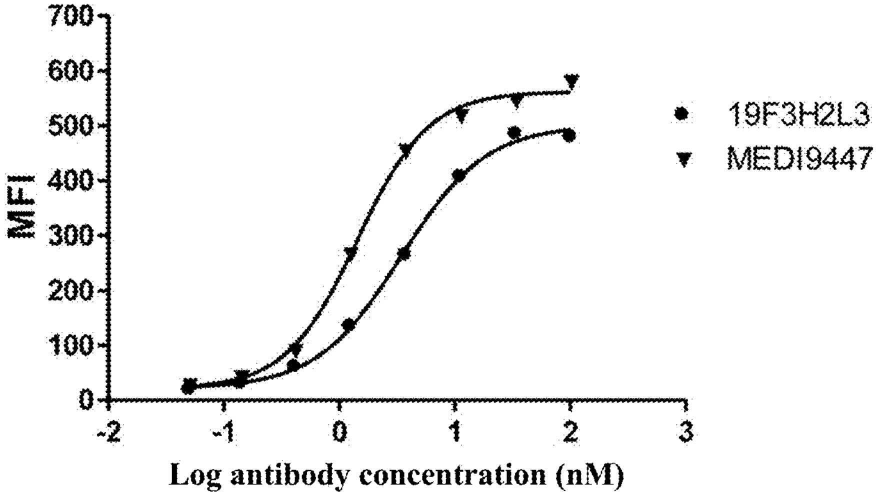
FIG. 4. Binding activity of 19F3H2L3 to CD73 on the surface of MDA-MB-231 cells determined by FACS.

Results are shown in Table 3 and FIG. 4, the binding ability of 19F3H2L3 to CD73 endogenously expressed in MDA-MB-231 is comparable to that of the positive drug MEDI9447 for the same target, and the binding is in a dose-dependent relationship. Under the same experimental conditions, $EC_{50}$ of 19F3H2L3 binding to CD73 endogenously expressed in MDA-MB-231 is 3.423 nM, and $EC_{50}$ of MEDI9447 binding to CD73 endogenously expressed in MDA-MB-231 is 1.433 nM.

The above experimental results show that the binding activity of 19F3H2L3 to CD73 endogenously expressed in MDA-MB-231 is comparable to that of the positive drug MEDI9447 for the same target under the same experimental conditions, indicating that 19F3H2L3 has the function of effectively binding to CD73.

TABLE 3

| Binding ability of 19F3H2L3 to CD73 on the surface of MDA-MB-231 cells determined by FACS | | | | | | | | | |
|---|---|---|---|---|---|---|---|---|---|
| | Absorbance (nM) | | | | | | | | |
| | 0.05 | 0.14 | 0.41 | 1.23 | 3.70 | 11.11 | 33.33 | 100.00 | $EC_{50}$ |
| MEDI9447 | 28.38 | 43.18 | 90.96 | 266.72 | 454.45 | 518.94 | 545.63 | 580.76 | 1.433 |
| 19F3H2L3 | 20.04 | 31.49 | 61.09 | 135.31 | 264.86 | 407.09 | 485.32 | 480.42 | 3.423 |

Example 7. Determination of Inhibitory Activity of Anti-CD73 Antibody on Enzyme Activity of CD73 Endogenously Expressed in Cells 1. Detection of Inhibitory Activity of Anti-CD73 Antibody on Enzyme Activity of CD73 Endogenously Expressed in MDA-MB-231 Cells The experimental procedures were as follows. MDA-MB-231 cells in logarithmic phase in good condition were taken, resuspended in a serum-free RPMI-1640 culture solution, and then counted. The MDA-MB-231 cells were seeded into a 96-well plate at $3\times10^4$ cells/100 μL/well. The antibody was diluted with the serum-free RPMI-1640 culture solution at an initial concentration of 200 μg/mL (serial 2.5-fold dilution). The antibody was added to the 96-well plate at 50 μL/well, and the plate was incubated at 37° C. for 1 hour. After 1 hour, 50 μL of RPMI-1640-diluted 600 μM AMP was added to each well. After 3 hours, 25 μL of cell culture supernatant was taken and transferred to a new 96-well plate, and 25 μL of 100 μM ATP was added to each well. 50 μL of CTG (CellTiter-Glo® One Solution Assay, promega, Cat. No. G8461) color developing solution was added to each well for color development, and data were read by a multi-label microplate tester (PerkinElmer 2140-0020).

Figure 5:
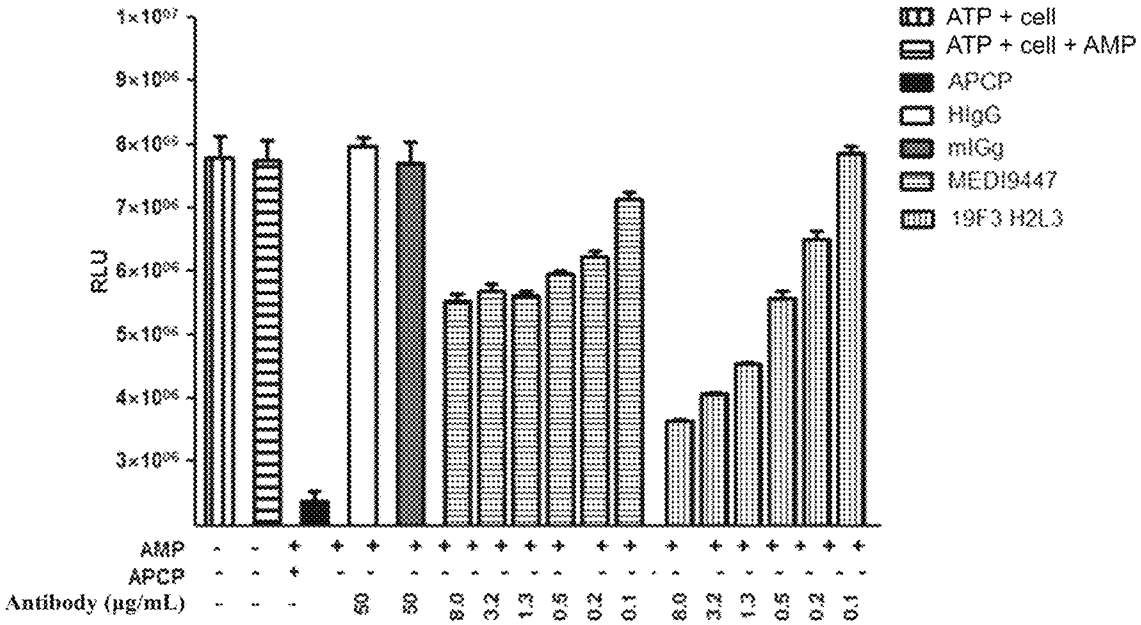
FIG. 5. Detection results of enzyme activity of anti-CD73 antibody added to MDA-MB-231 cells.

Experimental results: as shown in FIG. 5, both 19F3H2L3 and the positive control drug MEDI9447 for the same target showed dose-dependent inhibition of the activity of CD73 endogenously expressed in MDA-MB-231 converting AMP into adenosine A through enzyme catalysis, thereby reducing the produced mean fluorescence intensity RLU produced in a dose-dependent manner.

The above experimental results show that the added AMP can be subjected to enzyme catalysis of CD73 endogenously expressed on the cell surface by MDA-MB-231 and then converted into adenosine A under the condition of no CD73 antibody treatment, so that the inhibition of luciferase activity is relieved. However, after addition of the antibody, as CD73 was bound by the antibody, its enzymatic activity was reduced, so that AMP could not be converted into adenosine. It is suggested that the anti-CD73 antibody effectively inhibits the enzyme activity reaction of CD73 in a non-substrate competition mode and reduces the production of adenosine.

2. Determination of Enzyme Activity by Addition of Anti-CD73 Antibody to U87-MG Cells The experimental procedures were as follows. U87-MG cells in logarithmic phase in good condition were taken, resuspended in a serum-free RPMI-1640 culture solution, and then counted. The U87-MG cells were seeded into a 96-well plate at $3\times10^4$ cells/100 μL/well. The antibody was diluted with the serum-free RPMI-1640 culture solution at an initial concentration of 200 μg/mL (serial 2.5-fold dilution). The antibody was added to the 96-well plate at 50 μL/well, and the plate was incubated at 37° C. for 1 hour. After 1 hour, 50 μL of RPMI-1640-diluted 600 μM AMP was added to each well. After 3 hours, 25 μL of cell culture supernatant was taken and transferred to a new 96-well plate, and 25 μL of 100 μM ATP was added to each well. 50 μL of CTG (CellTiter-Glo® One Solution Assay, promega, Cat. No. G8461) color developing solution was added to each well for color development, and data were read by a multi-label microplate tester (PerkinElmer 2140-0020).

Figure 6:
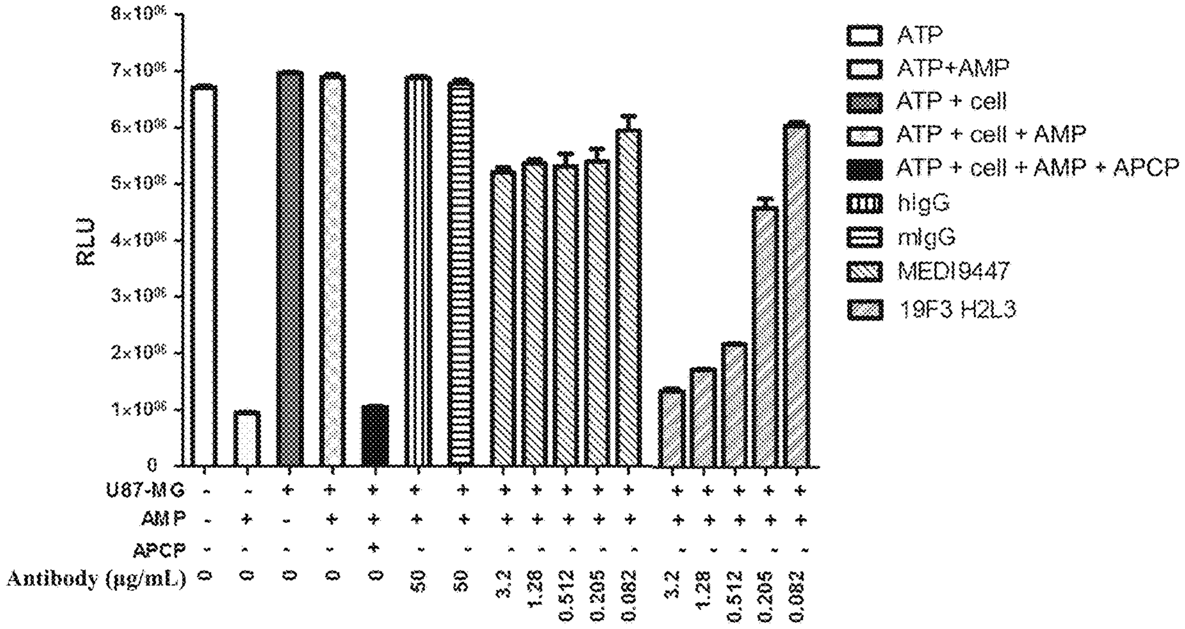
FIG. 6. Detection results of enzyme activity of anti-CD73 antibody added to U87-MG cells.

Experimental results: as shown in FIG. 6, both 19F3H2L3 and the positive control drug MEDI9447 for the same target showed dose-dependent inhibition of the activity of CD73 endogenously expressed in MDA-MB-231 converting AMP into adenosine through enzyme catalysis, thereby reducing the produced mean fluorescence intensity RLU produced in a dose-dependent manner.

The above experimental results show that the added AMP can be subjected to enzyme catalysis of CD73 endogenously expressed on the cell surface by U87-MG and then converted into adenosine under the condition of no CD73 antibody treatment, so that the inhibition of luciferase activity is relieved. However, after addition of the antibody, as CD73 was bound by the antibody, its enzymatic activity was reduced, so that AMP could not be converted into adenosine. It is suggested that the anti-CD73 antibody effectively inhibits the enzyme activity reaction of CD73 in a non-substrate competition mode and reduces the production of adenosine.

Example 8. Dynamic Affinity Determination of Anti-CD73 Antibodies and FcγRIIIa Mediating Antibody-Dependent Cytotoxic Effects The sample dilution buffer was PBS (0.02% Tween-20, 0.1% BSA, pH 7.4). 0.5 μg/mL FcγRIIIa (from Sino Biological, also known as CD16a) was immobilized on the SA sensor for 120 s. The sensor was equilibrated in a buffer for 60 s, and the binding of the immobilized CD16a on the sensor to the antibodies at concentrations of 31.3-500 nM (serial two-fold dilution) was determined for 60 s. The antibody-antigen was dissociated in buffer for 60 s. The sensor was refreshed with 10 mM NaOH. The detection temperature was 30° C. and the frequency was 0.6 Hz. The data were analyzed by 1:1 model fitting to obtain affinity constants. As shown in Table 4, 19F3H2L3(hG1DM) did not bind to FcγRIIIa, whereas MEDI9447 had binding activity to FcγRIIIa, indicating that 19F3H2L3(hG1DM) had a lower risk of causing antibody-dependent cytotoxic effects in CD73-expressing cells, whereas MEDI9447 had a risk of causing antibody-dependent cytotoxic effects.

CD73 is abundantly expressed in vascular endothelium and normal tissues, and binds to FcγRIIIa to mediate antibody-dependent cytotoxic effects, resulting in damage to vascular endothelial cells and normal tissues, which has significant effect on the safety of antibody drugs.

TABLE 4

Dynamic affinity determination of anti-CD73 antibodies and FcγRIIIa mediating antibody-dependent cytotoxic effects

| | KD (M) | kon (1/Ms) | Standard error (kon) | Kdis (1/s) | Standard error (kdis) |
|---|---|---|---|---|---|
| 19F3H2L3(hG1DM) | N/A | N/A | N/A | N/A | N/A |
| MEDI9447 | 1.41E−07 | 2.43E+05 | 4.36E+04 | 3.42E−02 | 2.08E−03 |
| Wild-type IgG1 antibody | 1.25E−07 | 1.76E+05 | 2.22E+04 | 2.20E−02 | 1.11E−03 |

KD = kdis/kon

SEQUENCE LISTING

The nucleotide sequence of the heavy chain variable region of 19F3 with CDR sequences underlined:

(SEQ ID NO: 1)

GAGGTGCAGCTGCAGCAGTCCGGACCAGAGCTGGTGAAGCCTGGCGCC

TCCATGCGGATGTCTTGTAAGGCCTCTGGCTACAGCTTCACCGGCTATA

CAATGAACTGGGTGAAGCAGTCTCACGGCAAGAATCTGGAGTGGATCG

GCCTGATCAACCCTTACAATGCCGGCACCAGCTATAACCAGAAGTTTA

AGGGCAAGGCCACCCTGACAGTGGACAAGAGCTCCTCTACCGCCTACA

TGGAGCTGCTGTCCCTGACATCTGAGGATAGCGCCGTGTACTATTGCGC

CCGGTCCGAGTACAGATATGGCGGCGACTACTTTGATTATTGGGGCCA

GGGCACCACACTGACAGTGAGCTCC

The amino acid sequence of the heavy chain variable region of 19F3 with CDR sequences underlined:

(SEQ ID NO: 2)

EVQLQQSGPELVKPGASMRMSCKASGYSFTGYTMNWVKQSHGKNLEWI

GLINPYNAGTSYNQKFKGKATLTVDKSSSTAYMELLSLTSEDSAVYYC

ARSEYRYGGDYFDYWGQGTTLTVSS

The nucleotide sequence of the light chain variable region of 19F3 with CDR sequences underlined:

(SEQ ID NO: 3)

GACATCGTGATGACCCAGTCTCCAAGCTCCCTGGCAATGAGCGTGGGA

CAGAAGGTGACAATGTCTTGTAAGTCTAGCCAGAGCCTGCTGAACTCCT

CTAATCAGAAGAACTACCTGGCCTGGTATCAGCAGAAGCCAGGCCAGT

CTCCCAAGCTGCTGGTGTACTTTGCCAGCACCAGGGAGTCCGGAGTGCC

TGACAGATTCATCGGCTCCGGCTCTGGCACAGACTTCACCCTGACAATC

AGCTCCGTGCAGGCAGAGGACCTGGCAGATTATTTCTGCCAGCAGCAC

TACGACACCCCTTATACATTTGGCGGCGGCACCAAGCTGGAGATCAAG

The amino acid sequence of the light chain variable region of 19F3 with CDR sequences underlined:

(SEQ ID NO: 4)

DIVMTQSPSSLAMSVGQKVTMSCKSSQSLLNSSNQKNYLAWYQQKPGQSP

KLLVYFASTRESGVPDRFIGSGSGTDFTLTISSVQAEDLADYFCQQHYDT

PYTFGGGTKLEIK

-continued

The nucleotide sequence of the heavy chain variable region of 19F3H1L1 with CDR sequences underlined:

(SEQ ID NO: 5)

CAGGTGCAGCTGCAGCAGTCTGGAGCAGAGGTGGTGAAGCCAGGAGCC

TCTATGAAGATGAGCTGTAAGGCCAGCGGCTACTCCTTCACCGGCTATA

CAATGAACTGGGTGAAGCAGGCCCACGGCCAGAATCTGGAGTGGATCG

GCCTGATCAACCCTTACAATGCCGGCACCTCTTATAACCAGAAGTTTCA

GGGCAAGGCCACCCTGACAGTGGACAAGTCCACCTCTACAGCCTACAT

GGAGCTGAGCTCCCTGCGGAGCGAGGATACAGCCGTGTACTATTGCGC

CCGGTCCGAGTACAGATATGGCGGCGACTACTTTGATTATTGGGGCCA

GGGCACCACACTGACCGTGTCTAGC

The amino acid sequence of the heavy chain variable region of 19F3H1L1 with CDR sequences underlined:

(SEQ ID NO: 6)

QVQLQQSGAEVVKPGASMKMSCKASGYSFTGYTMNWVKQAHGQNLEWI

GLINPYNAGTSYNQKFQGKATLTVDKSTSTAYMELSSLRSEDTAVYYC

ARSEYRYGGDYFDYWGQGTTLTVSS

The nucleotide sequence of the light chain variable region of 19F3H1L1 with CDR sequences underlined:

(SEQ ID NO: 7)

GACATCGTGATGACCCAGTCCCCAAGCTCCCTGGCAATGTCTGTGGGA

GAGAGGGTGACAATGTCCTGTAAGTCTAGCCAGTCTCTGCTGAACTCCT

CTAATCAGAAGAACTACCTGGCCTGGTATCAGCAGAAGCCCGGCCAGG

CCCCTAAGCTGCTGGTGTACTTTGCCTCTACCAGGGAGAGCGGAGTGCC

AGACAGATTCTCTGGCAGCGGCTCCGGCACAGACTTCACCCTGACAAT

CAGCTCCGTGCAGGCAGAGGACCTGGCAGATTATTTCTGCCAGCAGCA

CTACGATACCCCCTATACATTTGGCGGCGGCACCAAGCTGGAGATCAA

G

The amino acid sequence of the light chain variable region of 19F3H1L1 with CDR sequences underlined:

(SEQ ID NO: 8)

DIVMTQSPSSLAMSVGERVTMSCKSSQSLLNSSNOKNYLAWYOOKPG

QAPKLLVYFASTRESGVPDRFSGSGSGTDFTLTISSVOAEDLADYFC

QQHYDTPYTFGGGTKLEIK

-continued

The nucleotide sequence of the heavy chain variable regions of 19F3H2L2 and 19F3H2L3 with CDR sequences underlined:

(SEQ ID NO: 9)

CAGGTGCAGCTGGTGCAGTCTGGAGCAGAGGTGGTGAAGCCAGGAGCC

TCTGTGAAGGTGAGCTGTAAGGCCAGCGGCTACTCCTTCACCGGCTATA

CAATGAACTGGGTGAGGCAGGCACCAGGACAGAATCTGGAGTGGATCG

GCCTGATCAACCCTTACAATGCCGGCACCTCTTATAACCAGAAGTTTCA

GGGCAAGGTGACCCTGACAGTGGACAAGTCCACCTCTACAGCCTACAT

GGAGCTGAGCTCCCTGCGGAGCGAGGATACAGCCGTGTACTATTGCGC

CCGGTCCGAGTACAGATATGGCGGCGACTACTTTGATTATTGGGGCCA

GGGCACCACACTGACCGTGTCTAGC

The amino acid sequence of the heavy chain variable regions of 19F3H2L2 and 19F3H2L3 with CDR sequences underlined:

(SEQ ID NO: 10)

QVQLVQSGAEVVKPGASVKVSCKASGYSFTGYTMNWVRQAPGQNLEWI

GLINPYNAGTSYNQKFQGKVTLTVDKSTSTAYMELSSLRSEDTAVYYC

ARSEYRYGGDYFDYWGQGTTLTVSS

The nucleotide sequence of the light chain variable region of 19F3H2L2 with CDR sequences underlined:

(SEQ ID NO: 11)

GACATCGTGATGACCCAGTCCCCAAGCTCCCTGGCCGTGTCTGTGGGAG

AGCGGGTGACAATCTCCTGTAAGTCTAGCCAGTCTCTGCTGAACTCCTC

TAATCAGAAGAACTACCTGGCCTGGTATCAGCAGAAGCCCGGCCAGGC

CCCTAAGCTGCTGATCTACTTCGCCTCTACCAGGGAGAGCGGAGTGCCA

GACAGATTCTCTGGCAGCGGCTCCGGCACAGACTTCACCCTGACAATC

AGCTCCGTGCAGGCAGAGGACGTGGCAGATTACTATTGCCAGCAGCAC

TACGATACCCCCTATACATTTGGCGGCGGCACCAAGCTGGAGATCAAG

The amino acid sequence of the light chain variable region of 19F3H2L2 with CDR sequences underlined:

(SEQ ID NO: 12)

DIVMTQSPSSLAVSVGERVTISCKSSQSLLNSSNQKNYLAWYQQKPGQ

APKLLIYFASTRESGVPDRFSGSGSGTDFTLTISSVQAEDVADYYC

QQHYDTPYTFGGGTKLEIK

The nucleotide sequence of the light chain variable region of 19F3H2L3:

(SEQ ID NO: 13)

GACATCGTGATGACCCAGTCCCCAAGCTCCCTGGCCGTGTCTGTGGGAG

AGCGGGTGACAATCTCCTGTAAGTCTAGCCAGTCTCTGCTGAACTCCTC

TAATCAGAAGAACTACCTGGCCTGGTATCAGCAGAAGCCCGGCCAGGC

CCCTAAGCTGCTGATCTACTTCGCCTCTACCAGGGAGAGCGGAGTGCCA

GACAGATTCTCTGGCAGCGGCTCCGGCACAGACTTCACCCTGACAATC

AGCTCCCTGCAGGCAGAGGACGTGGCCGTGTACTATTGCCAGCAGCAC

TACGATACCCCCTATACATTTGGCGGCGGCACCAAGCTGGAGATCAAG

-continued

The amino acid sequence of the light chain variable region of 19F3H2L3 with CDR sequences underlined:

(SEQ ID NO: 14)

DIVMTQSPSSLAVSVGERVTISCKSSQSLLNSSNQKNYLAWYQQKPGQ

APKLLIYFASTRESGVPDRFSGSGSGTDFTLTISSLQAEDVAVYYC

FQQHYDTPYTGGGTKLEIK

The CDR regions of 19F3, 19F3H1L1, 19F3H2L2 and 19F3H2L3

HCDR1:

(SEQ ID NO: 15)

GYSFTGYT

HCDR2:

(SEQ ID NO: 16)

INPYNAGT

HCDR3:

(SEQ ID NO: 17)

ARSEYRYGGDYFDY

LCDR1:

(SEQ ID NO: 18)

QSLLNSSNQKNY

LCDR2:

(SEQ ID NO: 19)

FAS

LCDR3:

(SEQ ID NO: 20)

QQHYDTPYT

The sequence of the heavy chain constant regions (330 aa, mutation sites are underlined in bold) of 19F3H1L1(hG1DM), 19F3H2L2(hG1DM) and 19F3H2L3(hG1DM):

(SEQ ID NO: 21)

ASTKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPKS

CDKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTCLV

KGFYPSDIAVEWESNGQPENNYKTTPPVLDSDGSFFLYSKLTVDKSRWQQ

GNVFSCSVMHEALHNHYTQKSLSLSPGK

The sequence of the light chain constant regions (107 aa) of 19F3H1L1(hG1DM), 19F3H2L2(hG1DM) and 19F3H2L3(hG1DM):

(SEQ ID NO: 22)

RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTKS

FNRGEC

The invention claimed is:

1. An anti-CD73 antibody or an antigen-binding fragment thereof, wherein according to Kabat, Chothia or IMGT numbering system, the anti-CD73 antibody comprises:

HCDR1, HCDR2 and HCDR3 contained in a heavy chain variable region set forth in SEQ ID NO: 10; and LCDR1, LCDR2 and LCDR3 contained in a light chain variable region set forth in SEQ ID NO: 14.

2. The anti-CD73 antibody or the antigen-binding fragment thereof according to claim 1, wherein the antibody comprises a heavy chain variable region and a light chain variable region, the heavy chain variable region of the antibody comprises a sequence having at least sequence identity to SEQ ID NO: 2, and the light chain variable region of the antibody comprises a sequence having at least 90% sequence identity to SEQ ID NO: 4; or the heavy chain variable region of the antibody comprises a sequence having at least 90% sequence identity to SEQ ID NO: 6, and the light chain variable region of the antibody comprises a sequence having at least 93% sequence identity to SEQ ID NO: 8; or the heavy chain variable region of the antibody comprises a sequence having at least 85% sequence identity to SEQ ID NO: 10, and the light chain variable region of the antibody comprises a sequence having at least 92% sequence identity to SEQ ID NO: 12; or the heavy chain variable region of the antibody comprises a sequence having at least 85% sequence identity to SEQ ID NO: 10, and the light chain variable region of the antibody comprises a sequence having at least 90% sequence identity to SEQ ID NO: 14.

3. The anti-CD73 antibody or the antigen-binding fragment thereof according to claim 1, wherein the heavy chain variable region of the antibody comprises an amino acid sequence set forth in SEQ ID NO: 2, and the light chain variable region of the antibody comprises an amino acid sequence set forth in SEQ ID NO: 4;

the heavy chain variable region of the antibody comprises an amino acid sequence set forth in SEQ ID NO: 6, and the light chain variable region of the antibody comprises an amino acid sequence set forth in SEQ ID NO: 8;

the heavy chain variable region of the antibody comprises an amino acid sequence set forth in SEQ ID NO: 10, and the light chain variable region of the antibody comprises an amino acid sequence set forth in SEQ ID NO: 12; or the heavy chain variable region of the antibody comprises an amino acid sequence set forth in SEQ ID NO: 10, and the light chain variable region of the antibody comprises an amino acid sequence set forth in SEQ ID NO: 14.

4. The anti-CD73 antibody or the antigen-binding fragment thereof according to claim 1, wherein the antibody comprises a heavy chain constant region having a sequence set forth in SEQ ID NO: 21, and a light chain constant region having a sequence set forth in SEQ ID NO: 22; or the heavy chain constant region is Ig gamma-1 chain C region, ACCESSION: P01857 as set forth in SEQ ID NO: 23, and the light chain constant region is Ig kappa chain C region, ACCESSION: P01834 as set forth in SEQ ID NO: 24.

5. The anti-CD73 antibody or the antigen-binding fragment thereof according to claim 1, wherein the antibody is a monoclonal antibody, a humanized antibody, a chimeric antibody or a multispecific antibody.

6. The anti-CD73 antibody or the antigen-binding fragment thereof according to claim 1, wherein the antigen-binding fragment is selected from Fab, Fab', $F(ab')_2$, Fv, Fab/c, a single chain antibody, a humanized antibody, a chimeric antibody and a bispecific antibody.

7. An isolated polypeptide, selected from the group consisting of:

(1) an isolated polypeptide, comprising the sequences set forth in SEQ ID NO: 15, SEQ ID NO: 16 and SEQ ID NO: 17, wherein the polypeptide specifically binds to CD73 as a part of an anti-CD73 antibody, and the antibody further comprises the sequences set forth in SEQ ID NO: 18, SEQ ID NO: 19 and SEQ ID NO: 20;

(2) an isolated polypeptide, comprising the sequences set forth in SEQ ID NO: 18, SEQ ID NO: 19 and SEQ ID NO: 20, wherein the polypeptide specifically binds to CD73 as a part of an anti-CD73 antibody, and the antibody further comprises the sequences set forth in SEQ ID NO: 15, SEQ ID NO: 16 and SEQ ID NO: 17;

(3) an isolated polypeptide, comprising a sequence set forth in SEQ ID NO: 2 or a sequence having at least 85% sequence identity to the sequence set forth in SEQ ID NO: 2, wherein the polypeptide specifically binds to CD73 as a part of an anti-CD73 antibody, and the antibody further correspondingly comprises a sequence set forth in SEQ ID NO: 4, or a sequence having at least 90% sequence identity to the sequence set forth in SEQ ID NO: 4, wherein the isolated polypeptide comprises the sequences set forth in SEQ ID NO: 15, SEQ ID NO: 16 and SEQ ID NO: 17, and the antibody further comprises the sequences set forth in SEQ ID NO: 18, SEQ ID NO: 19 and SEQ ID NO: 20;

(4) an isolated polypeptide, comprising a sequence set forth in SEQ ID NO: 4, or a sequence having at least 90% sequence identity to the sequence set forth in SEQ ID NO:4, wherein the polypeptide specifically binds to CD73 as a part of an anti-CD73 antibody, and the antibody further correspondingly comprises a sequence set forth in SEQ ID NO: 2, or a sequence having at least 85% sequence identity to the sequence set forth in SEQ ID NO: 2, wherein the isolated polypeptide comprises the sequences set forth in SEQ ID NO: 18, SEQ ID NO: 19 and SEQ ID NO: 20, and the antibody further comprises the sequences set forth in SEQ ID NO: 15, SEQ ID NO: 16 and SEQ ID NO: 17;

(5) an isolated polypeptide, comprising a sequence set forth in SEQ ID NO: 10, or a sequence having at least 85% sequence identity to the sequence set forth in SEQ ID NO: 10, wherein the polypeptide specifically binds to CD73 as a part of an anti-CD73 antibody, and the antibody further correspondingly comprises a sequence set forth in SEQ ID NO: 14, or a sequence having at least 90% sequence identity to the sequence set forth in SEQ ID NO: 14, wherein the isolated polypeptide comprises the sequences set forth in SEQ ID NO: 15, SEQ ID NO: 16 and SEQ ID NO: 17, and the antibody further comprises the sequences set forth in SEQ ID NO: 18, SEQ ID NO: 19 and SEQ ID NO: 20;

(6) an isolated polypeptide, comprising a sequence set forth in SEQ ID NO: 14, or a sequence having at least 90% sequence identity to the sequence set forth in SEQ ID NO: 14, wherein the polypeptide specifically binds to CD73 as a part of an anti-CD73 antibody, and the antibody further correspondingly comprises a sequence set forth in SEQ ID NO: 10, or a sequence having at least 85% sequence identity to the sequence set forth in SEQ ID NO: 10, wherein the isolated polypeptide comprises the sequences set forth in SEQ ID NO: 18, SEQ ID NO: 19 and SEQ ID NO: 20, and the antibody further comprises the sequences set forth in SEQ ID NO: 15, SEQ ID NO: 16 and SEQ ID NO: 17;

(7) an isolated polypeptide, comprising a sequence set forth in SEQ ID NO: 6, or a sequence having at least 90% sequence identity to the sequence set forth in SEQ ID NO: 6, wherein the polypeptide specifically binds to CD73 as a part of an anti-CD73 antibody, and the antibody further correspondingly comprises a sequence set forth in SEQ ID NO: 8, or a sequence having at least 93% sequence identity to the sequence set forth in SEQ ID NO:8, wherein the isolated polypeptide comprises the sequences set forth in SEQ ID NO: 15, SEQ ID NO: 16 and SEQ ID NO: 17, and the antibody further comprises the sequences set forth in SEQ ID NO: 18, SEQ ID NO: 19 and SEQ ID NO: 20;

(8) an isolated polypeptide, comprising a sequence set forth in SEQ ID NO: 8, or a sequence having at least 93% sequence identity to the sequence set forth in SEQ ID NO: 8, wherein the polypeptide specifically binds to CD73 as a part of an anti-CD73 antibody, and the antibody further correspondingly comprises a sequence set forth in SEQ ID NO:6, or a sequence having at least 90% sequence identity to the sequence set forth in SEQ ID NO:6, wherein the isolated polypeptide comprises the sequences set forth in SEQ ID NO: 18, SEQ ID NO: 19 and SEQ ID NO: 20, and the antibody further comprises the sequences set forth in SEQ ID NO: 15, SEQ ID NO: 16 and SEQ ID NO: 17;

(9) an isolated polypeptide, comprising a sequence set forth in SEQ ID NO: 10, or a sequence having at least 85% sequence identity to the sequence set forth in SEQ ID NO: 10, wherein the polypeptide specifically binds to CD73 as a part of an anti-CD73 antibody, and the antibody further correspondingly comprises a sequence set forth in SEQ ID NO:12, or a sequence having at least 92% sequence identity to the sequence set forth in SEQ ID NO:12, wherein the isolated polypeptide comprises the sequences set forth in SEQ ID NO: 15, SEQ ID NO: 16 and SEQ ID NO: 17, and the antibody further comprises the sequences set forth in SEQ ID NO: 18, SEQ ID NO: 19 and SEQ ID NO: 20; and

(10) an isolated polypeptide, comprising a sequence set forth in SEQ ID NO:12, or a sequence having at least 92% sequence identity to the sequence set forth in SEQ ID NO: 12, wherein the polypeptide specifically binds to CD73 as a part of an anti-CD73 antibody, and the antibody further correspondingly comprises a sequence set forth in SEQ ID NO: 10, or a sequence having at least 85% sequence identity to the sequence set forth in SEQ ID NO:10, wherein the isolated polypeptide comprises the sequences set forth in SEQ ID NO: 18, SEQ ID NO: 19 and SEQ ID NO: 20, and the antibody further comprises the sequences set forth in SEQ ID NO: 15, SEQ ID NO: 16 and SEQ ID NO: 17.

8. A nucleic acid molecule, encoding the antibody or the antigen-binding fragment thereof according to claim 1.

9. A nucleic acid molecule, encoding the isolated polypeptide according to claim 7.

10. The antibody or the antigen-binding fragment thereof according to claim 1, contained in a conjugate, a fusion protein, a multispecific antibody, a pharmaceutical composition, or a kit, wherein the conjugate further comprises a conjugated moiety, the conjugated moiety is a purification tag or a detectable label.

11. The antibody or the antigen-binding fragment according to claim 1 for treating or diagnosing tumors.

12. A hybridoma cell line, selected from:

LT014, deposited at China Center for Type Culture Collection (CCTCC) with the accession number of CCTCC NO: C2018137.

13. The anti-CD73 antibody or an antigen-binding fragment thereof according to claim 1, wherein according to an IMGT numbering system, the anti-CD73 antibody comprises:

HCDR1, comprising an amino acid sequence set forth in SEQ ID NO: 15,

HCDR2, comprising an amino acid sequence set forth in SEQ ID NO: 16,

HCDR3, comprising an amino acid sequence set forth in SEQ ID NO: 17,

LCDR1, comprising an amino acid sequence set forth in SEQ ID NO: 18,

LCDR2, comprising an amino acid sequence set forth in SEQ ID NO: 19, and

LCDR3, comprising an amino acid sequence set forth in SEQ ID NO: 20.

14. The anti-CD73 antibody or the antigen-binding fragment thereof according to claim 1, wherein the antibody comprises a heavy chain variable region set forth in SEQ ID NO: 10, a light chain variable region set forth in SEQ ID NO: 14, a heavy chain constant region set forth in SEQ ID NO:21 and a light chain constant region set forth in SEQ ID NO:22.

15. The anti-CD73 antibody or the antigen-binding fragment thereof according to claim 10, wherein the multispecific antibody is a bispecific antibody, or the conjugated moiety is a radioisotope, a fluorescent substance, a chemiluminescent substance, a colored substance, polyethylene glycol or an enzyme, or the pharmaceutical composition further comprises a pharmaceutically acceptable carrier and/or excipient, or the kit further comprises a secondary antibody specifically recognizing the anti-CD73 antibody or the antigen-binding fragment thereof.

16. The anti-CD73 antibody or the antigen-binding fragment thereof according to claim 10, wherein the pharmaceutical composition is in a form suitable for administration by subcutaneous injection, intradermal injection, intravenous injection, intramuscular injection or intralesional injection.

17. The antibody or the antigen-binding fragment thereof of claim 11, wherein the tumor is solid tumor.

18. The antibody or the antigen-binding fragment thereof of claim 11, wherein the tumor is non-small cell lung cancer, prostate cancer, triple-negative breast cancer, ovarian cancer, colorectal cancer, gastric cancer, melanoma, head and neck cancer, renal cell carcinoma or pancreatic ductal adenocarcinoma.

19. The antibody or the antigen-binding fragment thereof of claim 18, wherein the colorectal cancer is colorectal cancer microsatellite stability, or the prostate cancer is metastatic castration-resistant prostate cancer.

* * * * *